(12) United States Patent
Park et al.

(10) Patent No.: US 10,306,873 B2
(45) Date of Patent: Jun. 4, 2019

(54) EXPRESSION CASSETTE AND VECTOR COMPRISING ALZHEIMER'S DISEASE-RELATED MUTANT GENES AND CELL LINE TRANSFORMED BY MEANS OF SAME

(71) Applicant: JEJU National University Industry—Academic Cooperation Foundation, Jeju-si, Jeju-do (KR)

(72) Inventors: Se Pill Park, Seoul (KR); Young Sok Choi, Seoul (KR); Eun Young Kim, Seoul (KR); Young Ho Kim, Gyeonggi-do (KR); Hyun Seok Hong, Gyeonggi-do (KR); Chan Kyu Park, Seoul (KR); Mi Seon Park, Seoul (KR)

(73) Assignee: Jeju National University Industry-Academic Cooperation Foundation, Jeju-si, Jeju-do (KR)

( * ) Notice: Subject to any disclaimer, the term of this patent is extended or adjusted under 35 U.S.C. 154(b) by 0 days.

(21) Appl. No.: 15/303,287

(22) PCT Filed: Apr. 16, 2015

(86) PCT No.: PCT/KR2015/003833
§ 371 (c)(1),
(2) Date: Oct. 11, 2016

(87) PCT Pub. No.: WO2015/160199
PCT Pub. Date: Oct. 22, 2015

(65) Prior Publication Data
US 2017/0112109 A1 Apr. 27, 2017

(30) Foreign Application Priority Data
Apr. 17, 2014 (KR) ........................ 10-2014-0046059

(51) Int. Cl.
| C07H 21/04 | (2006.01) |
| C12N 15/63 | (2006.01) |
| A01K 67/00 | (2006.01) |
| A01K 67/027 | (2006.01) |
| C12N 15/85 | (2006.01) |
| C07K 14/47 | (2006.01) |
| C12N 7/00 | (2006.01) |
| C12N 15/86 | (2006.01) |
| A61K 31/70 | (2006.01) |
| C07K 14/49 | (2006.01) |

(52) U.S. Cl.
CPC ...... *A01K 67/0278* (2013.01); *A01K 67/0273* (2013.01); *C07K 14/4711* (2013.01); *C12N 7/00* (2013.01); *C12N 15/8509* (2013.01); *C12N 15/86* (2013.01); *A01K 2207/15* (2013.01); *A01K 2217/052* (2013.01); *A01K 2217/072* (2013.01); *A01K 2217/203* (2013.01); *A01K 2227/10* (2013.01); *A01K 2227/108* (2013.01); *A01K 2267/0312* (2013.01); *C07K 14/49* (2013.01); *C12N 2015/8545* (2013.01); *C12N 2710/16143* (2013.01); *C12N 2740/10043* (2013.01); *C12N 2830/003* (2013.01)

(58) Field of Classification Search
CPC ........... A01K 67/0278; A01K 2227/10; A01K 2227/052; A01K 2217/072; C12N 15/86; C12N 15/8509; C12N 2830/003; C07K 14/4711
See application file for complete search history.

(56) References Cited

U.S. PATENT DOCUMENTS

| 6,420,534 B1 * | 7/2002 | Gurney | C07K 14/4711 435/226 |
| 7,018,799 B2 | 3/2006 | McCarthy et al. | |
| 7,098,374 B2 * | 8/2006 | Klein | A01K 67/0278 800/12 |
| 7,341,847 B2 * | 3/2008 | Wang | A61K 48/0058 435/320.1 |
| 7,479,579 B2 * | 1/2009 | LaFerla | A01K 67/0275 800/12 |
| 7,812,123 B2 | 10/2010 | Gurney et al. | |

(Continued)

FOREIGN PATENT DOCUMENTS

| WO | WO 2007/078599 A2 | 7/2007 |
| WO | WO 2008/150186 A1 | 12/2008 |
| WO | WO 2013/151736 A2 | 10/2013 |

OTHER PUBLICATIONS

Pico Caroni. Overexpression of growth-associated proteins in the neurons of adult trangenic mice. Journal of Neuroscience Methods 71:3-9, (Year: 1997).*

(Continued)

*Primary Examiner* — Quang Nguyen
(74) *Attorney, Agent, or Firm* — Gilberto M. Villacorta; Jason Mock; Foley & Lardner LLP

(57) ABSTRACT

The present invention relates to expression cassettes and vectors comprising Alzheimer's disease-related genes and a cell line transformed by the disclosed expression cassettes and vectors, and more specifically, the expression cassettes according to the present invention comprise amyloid precursor protein (APP), Tau protein, and presenilin-1 (PS1) genes associated with Alzheimer's disease so that mutant genes thereof can be simultaneously expressed. Additionally, the present invention relates to a cell line transformed by the disclosed expression cassettes or vectors comprising APP, Tau protein, and PS1 genes, and further, to an animal model transformed by the vectors or cell line.

5 Claims, 9 Drawing Sheets

Specification includes a Sequence Listing.

(56) References Cited

U.S. PATENT DOCUMENTS

| | | | |
|---|---|---|---|
| 8,236,490 B2* | 8/2012 | Roca et al. | |
| 8,389,794 B2* | 3/2013 | Jorgensen | A01K 67/0271 800/17 |
| 8,999,380 B2* | 4/2015 | Bancel | A61K 48/005 424/450 |
| 9,527,894 B2* | 12/2016 | Robitzki | C07K 14/47 |
| 2009/0018031 A1* | 1/2009 | Trinklein et al. | |
| 2016/0031976 A1* | 2/2016 | Seubert | C07K 16/18 424/133.1 |

OTHER PUBLICATIONS

Oddo, S. et al. "Triple-Transgenic Model of Alzheimer's Disease with Plaques and Tangles: Intracellular Aβ and Synaptic Dysfunction." Neuron, vol. 39, Jul. 31, 2003, pp. 409-421.

Liu, B. et al. "CMV Enhancer/human PGDF-β promoter for neuron-specific transgene expression." Gene Therapy, vol. 11, 2004, pp. 52-60.

Shin, J. et al. "Swedish mutation within amyloid precursor protein modulates global gene expression towards the pathogenesis of Alzheimer's disease." BMB Reports, vol. 43, No. 10, Oct. 2010, pp. 704-709.

Ahier, A. et al. "Simultaneous Expression of Multiple Proteins Under a Single Promoter in *Caenorhabditis elegans* Via a Versatile 2A-Based Toolkit." Genetics, vol. 196, Mar. 2014, pp. 605-613.

* cited by examiner

FIG. 4

```
Promotor site- PRODUCT SIZE: 171
OLIGO            start  len  tm     gc%    any 3' seq
LEFT PRIMER 477   477   25   55.14  52.00  5.00  3.00  GTGAGTACGTGTGACTGTGACTGAG  (SEQ ID NO: 35)
RIGHT PRIMER647        25   54.96  48.00  3.00  0.00  GTCAGTCACCCTGCTGTTACTATC   (SEQ ID NO: 36)

APP-2A-Tau site- PRODUCT SIZE: 120
OLIGO            start  len  tm     gc%    any 3' seq
LEFT PRIMER  30        25   54.88  40.00  4.00  2.00  AACCTACAAGTTCTTTGAGCAGATG  (SEQ ID NO: 37)
RIGHT PRIMER149        25   55.82  48.00  8.00  2.00  ATAGATCTAGGTCCAGGGTTCTCCT  (SEQ ID NO: 38)

Tau-2A-PS1 site- PRODUCT SIZE: 272
OLIGO            start  len  tm     gc%    any 3' seq
LEFT PRIMER   1        22   54.43  50.00  3.00  0.00  ATCTCAGCAATGTCTCCTCCAC     (SEQ ID NO: 39)
RIGHT PRIMER272        25   54.88  44.00  6.00  2.00  ATTCTGGCTACGTACAGTATTGCTC  (SEQ ID NO: 40)

Poly A site- PRODUCT SIZE: 222
OLIGO            start  len  tm     gc%    any 3' seq
LEFT PRIMER   6        25   55.37  40.00  8.00  0.00  GAGTTTGGACAAACCACAACTAGAA  (SEQ ID NO: 41)
RIGHT PRIMER227        25   54.76  40.00  4.00  1.00  GCAAAAGCGAAACTACTATATCCTG  (SEQ ID NO: 42)

Vector site after Poly A- PRODUCT SIZE: 172
OLIGO            start  len  tm     gc%    any 3' seq
LEFT PRIMER 613        25   55.95  40.00  5.00  2.00  CTTGACGATTTGACTTAGACATGC   (SEQ ID NO: 43)
RIGHT PRIMER784        25   54.98  36.00  6.00  0.00  TAATCCAGAGGTTGATTAACAGGAA  (SEQ ID NO: 44)
```

FIG. 7

|  | S0227 | | S0018 | | SW316 | |
|---|---|---|---|---|---|---|
| Recipient | 227 | 227 | 258 | 258 | 153 | 153 |
| AD (donor cell) | 239 | 239 | 248 | 252 | 161 | 161 |
| AD pig tissue 1 | 239 | 239 | 248 | 252 | 161 | 161 |
| AD pig tissue 2 | 239 | 239 | 248 | 252 | 161 | 161 |

SEQUENCE LISTING

```
<160> NUMBER OF SEQ ID NOS: 44

<210> SEQ ID NO 1
<211> LENGTH: 7785
<212> TYPE: DNA
<213> ORGANISM: Artificial Sequence
<220> FEATURE:
<223> OTHER INFORMATION: Description of Artificial Sequence: Synthetic
      modified Tet vector sequence

<400> SEQUENCE: 1
tttgaaagac cccacccgta ggtggcaagc tagcttaagt aacgccactt tgcaaggcat        60
```

```
ggaaaaatac ataactgaga atagaaaagt tcagatcaag gtcaggaaca aagaaacagc    120
tgaataccaa acaggatatc tgtggtaagc ggttcctgcc ccggctcagg gccaagaaca    180
gatgagacag ctgagtgatg ggccaaacag gatatctgtg gtaagcagtt cctgccccgg    240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca accctcact cggcgcgcca gtcttccgat agactgcgtc gcccgggtac    480
ccgtattccc aataaagcct cttgctgttt gcatccgaat cgtggtctcg ctgttccttg    540
ggagggtctc ctctgagtga ttgactaccc acgacggggg tctttcattt ggggctcgt    600 ccggatttg gagaccctg cccagggacc accgacccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccaggac tttggggggcc gttttttgtgg    840 cccgacctga ggaagggagt cgatgtgaa tccgaccccg tcaggatatg tggttctggt    900
aggagacgag aacctaaaac agttcccgcc tccgtctgaa tttttgcttt cggtttggaa    960
ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc ctacatcgtg acctgggaag ccttggcttt   1320 tgaccccct ccctgggtca agccctttgt acaccctaag cctccgcctc ctcttcctcc   1380
atccgccccg tctctccccc ttgaacctcc tcgttcgacc ccgcctcgat cctccctta   1440 tccagccctc actccttctc taggcgccgg aattccgatc tgatagcttg ccacaacccg   1500
taccaaagat ggatagatcc ggaaagcctg aactcaccgc gacgtctgtc gagaagtttc   1560
tgatcgaaaa gttcgacagc gtctccgacc tgatgcagct ctcggagggc gaagaatctc   1620
gtgctttcag cttcgatgta ggagggcgtg gatatgtcct gcgggtaaat agctgcgccg   1680
atggtttcta caaagatcgt tatgtttatc ggcactttgc atcggccgcg ctcccgattc   1740
cggaagtgct tgacattggg gaattcagcg agagcctgac ctattgcatc tcccgccgtg   1800
cacagggtgt cacgttgcaa gacctgcctg aaaccgaact gcccgctgtt ctgcagccgg   1860
tcgcggaggc catggatgcg atcgctgcgg ccgatcttag ccagacgagc gggttcggcc   1920
cattcggacc gcaaggaatc ggtcaataca ctacatggcg tgatttcata tgcgcgattg   1980
ctgatcccca tgtgtatcac tggcaaactg tgatggacga caccgtcagt gcgtccgtcg   2040
cgcaggctct cgatgagctg atgctttggg ccgaggactg ccccgaagtc cggcacctcg   2100
tgcacgcgga tttcggctcc aacaatgtcc tgacggacaa tggccgcata acagcggtca   2160
ttgactggag cgaggcgatg ttcggggatt cccaatacga ggtcgccaac atcttcttct   2220
ggaggccgtg gttggcttgt atggagcagc agacgcgcta cttcgagcgg aggcatccgg   2280
agcttgcagg atcgccgcgg ctccgggcgt atatgctccg cattggtctt gaccaactct   2340
atcagagctt ggttgacggc aatttcgatg atgcagcttg ggcgcagggt cgatgcgacg   2400
caatcgtccg atccggagcc gggactgtcg ggcgtacaca aatcgcccgc agaagcgcgg   2460
```

```
ccgtctggac cgatggctgt gtagaagtac tcgccgatag tggaaaccga cgccccagca   2520
ctcgtccgag ggcaaaggaa tagagtagat gccgaccgaa caagagctga tttcgagaac   2580
gcctcagcca gcaactcgcg cgagcctagc aaggcaaatg cgagagaacg gccttacgct   2640
tggtggcaca gttctcgtcc acagttcgct aagctcgctc ggctgggtcg cgggagggcc   2700
ggtcgcagtg attcaggccc ttctggattg tgttggtccc cagggcacga ttgtcatgcc   2760
cacgcactcg ggtgatctga ctgatcccgc agattggaga tcgccgcccg tgcctgccga   2820
ttgggtgcag atctatttaa ataccggtac gcgtatgcat ttaattaagt ttaaacatgc   2880
atcctgcagg gcggccgcct cgagagatcc cctcaggata tagtagtttc gcttttgcat   2940 agggagggg aaatgtagtc ttatgcaata ctcttgtagt cttgcaacat ggtaacgatg    3000
agttagcaac atgccttaca aggagagaaa aagcaccgtg catgccgatt ggtggaagta   3060
aggtggtacg atcgtgcctt attaggaagg caacagacgg gtctgacatg gattggacga   3120
accactgaat tccgcattgc agagatattg tatttaagtg cctagctcga tacagcaaac   3180
gccatttgac cattcaccac attggtgtgc acctccaagc ttgttaattc accatgtcta   3240
gactggacaa gagcaaagtc ataaacggcg ctctggaatt actcaatgga gtcggtatcg   3300
aaggcctgac gacaaggaaa ctcgctcaaa agctgggagt tgagcagcct accctgtact   3360
ggcacgtgaa gaacaagcgg gccctgctcg atgccctgcc aatcgagatg ctggacaggc   3420
atcataccca cttctgcccc ctggaaggcg agtcatggca agactttctg cggaacaacg   3480
ccaagtcatt ccgctgtgct ctcctctcac atcgcgacgg ggctaaagtg catctcggca   3540
cccgcccaac agagaaacag tacgaaaccc tggaaaatca gctcgcgttc ctgtgtcagc   3600
aaggcttctc cctggagaac gcactgtacg ctctgtccgc cgtgggccac tttacactgg   3660
gctgcgtatt ggaggaacag gagcatcaag tagcaaaaga ggaaagagag acacctacca   3720
ccgattctat gccccacttt ctgagacaag caattgagct gttcgaccgg cagggagccg   3780
aacctgcctt ccttttcggc ctggaactaa tcatatgtgg cctggagaaa cagctaaagt   3840
gcgaaagcgg cgggccggcc gacgcccttg acgattttga cttagacatg ctcccagccg   3900
atgcccttga cgactttgac cttgatatgc tgcctgctga cgctcttgac gattttgacc   3960
ttgacatgct ccccgggtaa ctaagtaagg atcaacatcg aattcgattt ctgttcctgt   4020
taatcaacct ctggattaca aaatttgtga agattgact ggtattctta actatgttgc    4080
tccttttacg ctatgtggat acgctgcttt aatgcctttg tatcatgcta ttgcttcccg   4140
tatggctttc attttctcct ccttgtataa atcctggttg ctgtctcttt atgaggagtt   4200
gtggcccgtt gtcaggcaac gtggcgtggt gtgcactgtg tttgctgacg caacccccac   4260 tggttgggc attgccacca cctgtcagct cctttccggg actttcgctt tccccctccc   4320
tattgccacg gcggaactca tcgccgcctg ccttgcccgc tgctggacag gggctcggct   4380
gttgggcact gacaattccg tggtgttgtc ggggaagctg acgtcctttc catggctgct   4440
cgcctgtgtt gccacctgga ttctgcgcgg gacgtccttc tgctacgtcc cttcggccct   4500
caatccagcg gaccttcctt cccgcggcct gctgccggct ctgcggcctc ttccgcgtct   4560
tcgccttcgc cctcagacga gtcggatctc cctttgggcc gctcccgc ctgtttcgcc     4620 tcgggctcaa tcactagtga attcgataaa ataaagatt ttattagtc tccagaaaaa     4680 ggggggaatg aaagacccca cctgtaggtt tggcaagcta gcttaagtaa cgccattttg   4740
caaggcatgg aaaaatacat aactgagaat agagaagttc agatcaaggt caggaacaga   4800
```

```
tggaacagct gaatatgggc caaacaggat atctgtggta agcagttcct gccccggctc    4860
agggccaaga acagatggaa cagctgaata tgggccaaac aggatatctg tggtaagcag    4920
ttcctgcccc ggctcagggc caagaacaga tggtcccag atgcggtcca gccctcagca    4980
gtttctagag aaccatcaga tgtttccagg gtgcccaag acctgaaat gaccctgtgc     5040 cttatttgaa ctaaccaatc agttcgcttc tcgcttctgt tcgcgcgctt ctgctccccg    5100
agctcaataa aagagcccac aaccctcac tcggggcgcc agtcctccga ttgactgagt    5160
cgcccgggta cccgtgtatc caataaaccc tcttgcagtt gcatccgact tgtggtctcg    5220
ctgttccttg ggagggtctc ctctgagtga ttgactaccc gtcagcgggg gtctttcatt    5280
tgggggctcg tccgggatcg ggagacccct gcccagggac caccgaccca ccaccgggag    5340
gtaagctggc tgcctcgcgc gtttcggtga tgacggtgaa aacctctgac acatgcagct    5400
cccggagacg gtcacagctt gtctgtaagc ggatgccggg agcagacaag cccgtcaggg    5460
cgcgtcagcg ggtgttggcg ggtgtcgggg cgcagccatg acccagtcac gtagcgatag    5520
cggagtgtat actggcttaa ctatgcggca tcagagcaga ttgtactgag agtgcaccat    5580
atgcggtgtg aaataccgca cagatgcgta aggagaaaat accgcatcag gcgctcttcc    5640
gcttcctcgc tcactgactc gctgcgctcg tcgttcggc tgcggcgagc ggtatcagct    5700
cactcaaagg cggtaatacg gttatccaca gaatcagggg ataacgcagg aaagaacatg    5760
tgagcaaaag gccagcaaaa ggccaggaac cgtaaaaagg ccgcgttgct ggcgtttttc    5820
cataggctcc gcccccctga cgagcatcac aaaaatcgac gctcaagtca gaggtggcga    5880
aacccgacag gactataaag ataccaggcg tttccccctg gaagctccct cgtgcgctct    5940
cctgttccga ccctgccgct taccggatac ctgtccgcct ttctcccttc gggaagcgtg    6000
gcgctttctc atagctcacg ctgtaggtat ctcagttcgg tgtaggtcgt tcgctccaag    6060
ctgggctgtg tgcacgaacc ccccgttcag cccgaccgct gcgccttatc cggtaactat    6120
cgtcttgagt ccaacccggt aagacacgac ttatcgccac tggcagcagc cactggtaac    6180
aggattagca gagcgaggta tgtaggcggt gctacagagt tcttgaagtg gtggcctaac    6240
tacggctaca ctagaaggac agtatttggt atctgcgctc tgctgaagcc agttaccttc    6300
ggaaaaagag ttggtagctc ttgatccggc aaacaaacca ccgctggtag cggtggtttt    6360
tttgtttgca agcagcagat tacgcgcaga aaaaaaggat ctcaagaaga tcctttgatc    6420
ttttctacgg ggtctgacgc tcagtggaac gaaaactcac gttaagggat tttggtcatg    6480
agattatcaa aaaggatctt cacctagatc cttttaaatt aaaaatgaag ttttaaatca    6540
atctaaagta tatatgagta aacttggtct gacagttacc aatgcttaat cagtgaggca    6600
cctatctcag cgatctgtct atttcgttca tccatagttg cctgactccc cgtcgtgtag    6660
ataactacga tacgggaggg cttaccatct ggccccagtg ctgcaatgat accgcgagac    6720
ccacgctcac cggctccaga tttatcagca ataaaccagc cagccggaag ggccgagcgc    6780
agaagtggtc ctgcaacttt atccgcctcc atccagtcta ttaattgttg ccgggaagct    6840
agagtaagta gttcgccagt taatagtttg cgcaacgttg ttgccattgc tgcaggcatc    6900
gtggtgtcac gctcgtcgtt tggtatggct tcattcagct ccggttccca acgatcaagg    6960
cgagttacat gatccccat gttgtgcaaa aaagcggtta gctccttcgg tcctccgatc    7020
gttgtcagaa gtaagttggc cgcagtgtta tcactcatgg ttatggcagc actgcataat    7080
tctcttactg tcatgccatc cgtaagatgc ttttctgtga ctggtgagta ctcaaccaag    7140
tcattctgag aatagtgtat gcggcgaccg agttgctctt gcccggcgtc aacacgggat    7200
```

```
aataccgcgc cacatagcag aactttaaaa gtgctcatca ttggaaaacg ttcttcgggg    7260
cgaaaactct caaggatctt accgctgttg agatccagtt cgatgtaacc cactcgtgca    7320
cccaactgat cttcagcatc tttacttc accagcgttt ctgggtgagc aaaaacagga    7380
aggcaaaatg ccgcaaaaaa gggaataagg gcgacacgga aatgttgaat actcatactc    7440
ttcctttttc aatattattg aagcatttat cagggttatt gtctcatgag cggatacata    7500
tttgaatgta tttagaaaaa taaacaaata ggggttccgc gcacatttcc ccgaaaagtg    7560
ccacctgacg tctaagaaac cattattatc atgacattaa cctataaaaa taggcgtatc    7620
acgaggccct ttcgtcttca agaattcata ccagatcacc gaaaactgtc ctccaaatgt    7680 gtcccctca cactcccaaa ttcgcgggct ctgcctctt agaccactct accctattcc    7740
ccacactcac cggagccaaa gccgcggccc ttccgtttct ttgct    7785
```

<210> SEQ ID NO 2
<211> LENGTH: 1510
<212> TYPE: DNA
<213> ORGANISM: Artificial Sequence
<220> FEATURE:
<223> OTHER INFORMATION: Description of Artificial Sequence: Synthetic
      human PDGF promoter sequence

<400> SEQUENCE: 2

```
gctgggacta caggagcttg ttaccacacc cagctccagt ttataaattc atctccagtt      60 tataaggag gaaaccgagg tactgagagg ttaaaaaacc ttcctgcaga cacttgtcca     120
gcaagtggcc actccaggat ttggaccaag gtgatgtgtc ttcaggctgt gtctctgcca     180
ctgtgccacg ctgctgggtg gtaggcagca gtgggtgggt gcctgcagtg gtctgtaaag     240
accacctgag atgtccttcc tcctctgttc caccctgtcc aggtccaaga agacagtcta     300
tgaagagaga gcaggtgtga ctctctcagt gtgctcctct gtgagaagca ggctgacatc     360
ccaaagggaa gggcggataa cagagacagt gcaagcggag gagatgaggg tgcctcaaag     420
ccgggaggct gggtgatgca ggagcctgcg tgtcccgagg ggggtgctgg gcccagtgtg     480
agtacgtgtg actgtgactg agacagtgtg actgctgaag gcaggacac agcagctccc     540 tgactggggg cagaaggcgt taactgtgtg aaggctggtt gtgggtgggt gggctctggg     600
cctcgaaccc gggggctgag ggagatagta acagcaggg tgactgacgg gaagatcatg     660
ttggtagccc tgcgaagatg ctgcagggct gtggggttt gtgtgacttt gcagttcaac     720
aaattcaaat tcagccaacg ctggcagggc ctgttgtgcc aggcaaccag ctaggaggag     780
gagactcgga cccagcttgc agctgaaggg cgctggctgc cgggttctgt gggttcacct     840
tgcggtgtct tcccttgcta acactgagtc cttacaatag ccccatctcc aggttgaggc     900
tagatggagg ggacagaggg aagtgacttg cccaaggtga cccaagctcc cgagtgccag     960
ggcaggatct gaattcaggc tctcagactg cagagcctga gtccctccct gccatgcctg    1020
tgccagggtg gaaatgtctg gtcctggagg ggagcgtgga ctcctggcct tggctctgga    1080
gacatccccc tagaccacgt gggctcctaa cctgtccatg gtcactgtgc tgaggggcgg    1140
gacggtgggt caccccctagt tcttttttcc ccagggccag attcatggac tgaagggttg    1200
ctcggctctc agagaccccc taagcgcccc gccctggccc caagccctcc cccagctccc    1260 gcgtccccc cctcctggcg ctgactccgg gccagaagag gaaaggctgt ctccaccccac    1320 ctctcgcact ctcccttctc ctttataaag gccggaacag ctgaaagggt ggcaacttct    1380
cctcctgcag ccgggagcgg cctgcctgcc tccctgcgca cccgcagcct ccccgctgc    1440
```

```
ctccctaggg ctccctccg gccgccagcg cccatttttc attccctaga tagagatact    1500
ttgcgcgcac                                                          1510

<210> SEQ ID NO 3
<211> LENGTH: 305
<212> TYPE: DNA
<213> ORGANISM: Artificial Sequence
<220> FEATURE:
<223> OTHER INFORMATION: Description of Artificial Sequence: Synthetic
      CMV enhancer sequence

<400> SEQUENCE: 3
gcgttacata acttacggta aatggcccgc ctggctgacc gcccaacgac ccccgcccat     60
tgacgtcaat aatgacgtat gttcccatag taacgccaat agggactttc cattgacgtc    120
aatgggtgga gtatttacgg taaactgccc acttggcagt acatcaagtg tatcatatgc    180
caagtacgcc ccctattgac gtcaatgacg gtaaatggcc cgcctggcat tatgcccagt    240
acatgacctt atgggacttt cctacttggc agtacatcta cgtattagtc atcgctatta    300
ccatg                                                               305

<210> SEQ ID NO 4
<211> LENGTH: 2085
<212> TYPE: DNA
<213> ORGANISM: Artificial Sequence
<220> FEATURE:
<223> OTHER INFORMATION: Description of Artificial Sequence: Synthetic
      human APPsw sequence

<400> SEQUENCE: 4
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct ctcgttcct gacaagtgca aattcttaca ccaggagagg    420
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca agtagtaga agtagcagag gaggaagaag tggctgaggt ggaagaagaa    720
gaagccgatg atgacgagga cgatgaggat ggtgatgagg tagaggaaga ggctgaggaa    780
ccctacgaag aagccacaga gagaaccacc agcattgcca ccaccaccac caccaccaca    840
gagtctgtgg aagaggtggt tcgagttcct acaacagcag ccagtacccc tgatgccgtt    900
gacaagtatc tcgagacacc tggggatgag aatgaacatg cccatttcca gaaagccaaa    960
gagaggcttg aggccaagca ccgagagaga atgtcccagg tcatgagaga atgggaagag   1020
gcagaacgtc aagcaaagaa cttgcctaaa gctgataaga aggcagttat ccagcatttc   1080
caggagaaag tggaatcttt ggaacaggaa gcagccaacg agagacagca gctggtggag   1140
acacacatgg ccagagtgga agccatgctc aatgaccgcc gccgcctggc cctggagaac   1200
```

```
tacatcaccg ctctgcaggc tgttcctcct cggcctcgtc acgtgttcaa tatgctaaag    1260
aagtatgtcc gcgcagaaca gaaggacaga cagcacaccc taaagcattt cgagcatgtg    1320
cgcatggtgg atcccaagaa agccgctcag atccggtccc aggttatgac acacctccgt    1380
gtgatttatg agcgcatgaa tcagtctctc tccctgctct acaacgtgcc tgcagtggcc    1440
gaggagattc aggatgaagt tgatgagctg cttcagaaag agcaaaacta ttcagatgac    1500
gtcttggcca acatgattag tgaaccaagg atcagttacg gaaacgatgc tctcatgcca    1560
tctttgaccg aaacgaaaac caccgtggag ctccttcccg tgaatggaga gttcagcctg    1620
gacgatctcc agccgtggca ttcttttggg gctgactctg tgccagccaa cacagaaaac    1680
gaagttgagc ctgttgatgc ccgccctgct gccgaccgag gactgaccac tcgaccaggt    1740
tctgggttga caaatatcaa gacggaggag atctctgaag tgaatctgga tgcagaattc    1800
cgacatgact caggatatga agttcatcat caaaaattgg tgttctttgc agaagatgtg    1860
ggttcaaaca aaggtgcaat cattggactc atggtgggcg tgttgtcat agcgacagtg    1920 gtcatcatca ccttggtgat gctgaagaag aaacagtaca catccattca tcatggtgtg    1980
gtggaggttg acgccgctgt cacccccagag gagcgccacc tgtccaatct gcagcagaac    2040
ggctacgaaa atccaaccta caagttcttt gagcagatgc agaac                     2085
```

<210> SEQ ID NO 5
<211> LENGTH: 1149
<212> TYPE: DNA
<213> ORGANISM: Artificial Sequence
<220> FEATURE:
<223> OTHER INFORMATION: Description of Artificial Sequence: Synthetic human Tau sequence

<400> SEQUENCE: 5

```
atggctgagc cccgccagga gttcgaagtg atggaagatc acgctgggac gtacgggttg      60
ggggacagga aagatcaggg gggctacacc atgcaccaag accaagaggg tgacacggac     120
gctggcctga agctgaaga agcaggcatt ggagacaccc ccagcctgga agacgaagct     180
gctggtcacg tgacccaagc tcgcatggtc agtaaaagca agacgggac tggaagcgat     240 gacaaaaaag ccaagggggc tgatggtaaa acgaagatcg ccacaccgcg gggagcagcc     300
cctccaggcc agaagggcca ggccaacgcc accaggattc agcaaaaaac cccgcccgct     360
ccaaagacac cacccagctc tggtgaacct ccaaaatcag gggatcgcag cggctacagc     420
agccccggct ccccaggcac tcccggcagc cgctcccgca cccgtccct tccaaccca     480 cccaccccggg agcccaagaa ggtggcagtg gtccgtactc cacccaagtc gccgtcttcc     540
gccaagagcc gcctgcagac agccccccgtg cccatgccag acctgaagaa tgtcaagtcc     600
aagatcggct ccactgagaa cctgaagcac cagccgggag cgggaaggt gcagataatt     660 aataagaagc tggatcttag caacgtccag tccaagtgtg gctcaaagga taatatcaaa     720
cacgtcctgg gaggcggcag tgtgcaaata gtctacaaac cagttgacct gagcaaggtg     780
acctccaagt gtggctcatt aggcaacatc catcataaac caggaggtgg ccaggtggaa     840
gtaaaatctg agaagcttga cttcaaggac agagtccagt cgaagattgg gtccctggac     900
aatatcaccc acgtccctgg cggaggaaat aaaaagattg aaaccacaa gctgaccttc     960 cgcgagaacg ccaaagccaa gacagaccac ggggcggaga tcgtgtacaa gtcgccagtg    1020
gtgtctgggg acacgtctcc acggcatctc agcaatgtct cctccaccgg cagcatcgac    1080
atggtagact cgcccccagct cgccacgcta gctgacgagg tgtctgcctc cctggccaag    1140
```

```
cagggtttg                                                      1149

<210> SEQ ID NO 6
<211> LENGTH: 1404
<212> TYPE: DNA
<213> ORGANISM: Artificial Sequence
<220> FEATURE:
<223> OTHER INFORMATION: Description of Artificial Sequence: Synthetic
      human PS1 sequence

<400> SEQUENCE: 6
atgacagagt tacctgcacc gttgtcctac ttccagaatg cacagatgtc tgaggacaac     60
cacctgagca atactgtacg tagccagaat gacaatagag aacggcagga gcacaacgac    120
agacggagcc ttggccaccc tgagccatta tctaatggac gaccccaggg taactcccgg    180
caggtggtgg agcaagatga ggaagaagat gaggagctga cattgaaata tggcgccaag    240
catgtgatca tgctctttgt ccctgtgact ctctgcatgg tggtggtcgt ggctaccatt    300
aagtcagtca gcttttatac ccggaaggat gggcagctaa tctataccccc attcacagaa   360 gataccgaga ctgtgggcca gagagccctg cactcaattc tgaatgctgc catcatgatc    420
agtgtcattt ttgtcctgac tatcctcctg gtggttctgt ataaatacag gtgctataag    480
gtcatccatg cctggcttat tatatcatct ctattgttgc tgttcttttt ttcattcatt    540
tacttggggg aagtgtttaa aacctataac gttgctgtgg actacattac tgttgcactc    600
ctgatctgga attttggtgt ggtgggaatg atttccattc actggaaagg tccacttcga    660
ctccagcagg catatctcat tatgattagt gccctcatgg ccctggtgtt tatcaagtac    720
ctccctgaat ggactgcgtg gctcatcttg gctgtgattt cagtatatga tttagtggct    780
gttttgtgtc cgaaaggtcc acttcgtatg ctggttgaaa cagctcagga gagaaatgaa    840
acgctttttc cagctgtcat ttactcctca caatggtgt ggttggtgaa tatggcagaa    900
ggagacccgg aagctcaaag gagagtatcc aaaaattcca gtataatgc agaaagcaca    960 gaaagggagt cacaagacac tgttgcagag aatgatgatg gcgggttcag tgaggaatgg    1020
gaagcccaga gggacagtca tctagggcct catcgctcta cacctgagtc acgagctgct    1080
gtccaggaac tttccagcag tatcctcgct ggtgaagacc cagaggaaag gggagtaaaa    1140
cttggattgg gagatttcat tttctacagt gttctggttg gtaaagcctc agcaacagcc    1200
agtggagact ggaacacaac catagcctgt tcgtagcca tattaattgg tttgtgcctt    1260
acattattac tccttgccat tttcaagaaa gcattgccag ctcttccaat ctccatcacc    1320
tttgggcttg ttttctactt tgccacagat tatcttgtac agccttttat ggaccaatta    1380
gcattccatc aatttatat ctag                                            1404

<210> SEQ ID NO 7
<211> LENGTH: 186
<212> TYPE: DNA
<213> ORGANISM: Artificial Sequence
<220> FEATURE:
<223> OTHER INFORMATION: Description of Artificial Sequence: Synthetic
      SV40 poly A sequence

<400> SEQUENCE: 7
agatacattg atgagtttgg acaaaccaca actagaatgc agtgaaaaaa atgctttatt     60
tgtgaaattt gtgatgctat tgctttattt gtaaccatta taagctgcaa taaacaagtt    120
aacaacaaca attgcattca ttttatgttt caggttcagg gggaggtgtg ggaggttttt    180
taattc                                                                186
```

```
<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence: Synthetic
      2A sequence

<400> SEQUENCE: 8
ggaagcggag ctactaactt cagcctgctg aagcaggctg agacgtggg ggagaaccct      60 ggacct                                                               66

<210> SEQ ID NO 9
<211> LENGTH: 14618
<212> TYPE: DNA
<213> ORGANISM: Artificial Sequence
<220> FEATURE:
<223> OTHER INFORMATION: Description of Artificial Sequence: Synthetic
      final construct pTet-CMVE-hPDGFb-APPsw-2A-Tau
      -2A-PS1 sequence

<400> SEQUENCE: 9
tttgaaagac cccacccgta ggtggcaagc tagcttaagt aacgccactt tgcaaggcat      60
ggaaaaatac ataactgaga atagaaaagt tcagatcaag gtcaggaaca agaaacagc     120 tgaataccaa acaggatatc tgtggtaagc ggttcctgcc ccggctcagg gccaagaaca    180
gatgagacag ctgagtgatg gccaaacag gatatctgtg gtaagcagtt cctgccccgg     240
ctcggggcca agaacagatg gtccccagat gcggtccagc cctcagcagt ttctagtgaa    300
tcatcagatg tttccagggt gccccaagga cctgaaaatg accctgtacc ttatttgaac    360
taaccaatca gttcgcttct cgcttctgtt cgcgcgcttc cgctctccga gctcaataaa    420
agagcccaca ccccctcact cggcgcgcca gtcttccgat agactgcgtc gcccgggtac    480
ccgtattccc aataaagcct cttgctgttt gcatccgaat cgtggtctcg ctgttccttg    540
ggagggtctc ctctgagtga ttgactaccc acgacggggg tctttcattt gggggctcgt    600
ccgggatttg gagaccccctg cccagggacc accgacccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccagggac tttggggggcc gttttttgtgg   840 cccgacctga ggaagggagt cgatgtgaa tccgaccccg tcaggatatg tggttctggt    900
aggagacgag aacctaaaac agttcccgcc tccgtctgaa ttttttgctttt cggttttggaa    960 ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc ctacatcgtg acctgggaag ccttggcttt   1320
tgacccccct ccctgggtca agccctttgt acaccctaag cctccgcctc ctcttcctcc   1380
atccgccccg tctctccccc ttgaacctcc tcgttcgacc ccgcctcgat cctccctta   1440 tccagccctc actccttctc taggcgccgg aattccgatc tgatagcttg ccacaacccg   1500
taccaaagat ggatagatcc ggaaagcctg aactcaccgc gacgtctgtc gagaagtttc   1560
```

```
tgatcgaaaa gttcgacagc gtctccgacc tgatgcagct ctcggagggc gaagaatctc    1620
gtgctttcag cttcgatgta ggagggcgtg gatatgtcct gcgggtaaat agctgcgccg    1680
atggtttcta caaagatcgt tatgtttatc ggcactttgc atcggccgcg ctcccgattc    1740
cggaagtgct tgacattggg gaattcagcg agagcctgac ctattgcatc tcccgccgtg    1800
cacagggtgt cacgttgcaa gacctgcctg aaaccgaact gcccgctgtt ctgcagccgg    1860
tcgcggaggc catggatgcg atcgctgcgg ccgatcttag ccagacgagc gggttcggcc    1920
cattcggacc gcaaggaatc ggtcaataca ctacatggcg tgatttcata tgcgcgattg    1980
ctgatcccca tgtgtatcac tggcaaactg tgatggacga caccgtcagt gcgtccgtcg    2040
cgcaggctct cgatgagctg atgctttggg ccgaggactg ccccgaagtc cggcacctcg    2100
tgcacgcgga tttcggctcc aacaatgtcc tgacggacaa tggccgcata acagcggtca    2160
ttgactggag cgaggcgatg ttcggggatt cccaatacga ggtcgccaac atcttcttct    2220
ggaggccgtg gttggcttgt atggagcagc agacgcgcta cttcgagcgg aggcatccgg    2280
agcttgcagg atcgccgcgg ctccgggcgt atatgctccg cattggtctt gaccaactct    2340
atcagagctt ggttgacggc aatttcgatg atgcagcttg ggcgcagggt cgatgcgacg    2400
caatcgtccg atccggagcc gggactgtcg ggcgtacaca aatcgcccgc agaagcgcgg    2460
ccgtctggac cgatggctgt gtagaagtac tcgccgatag tggaaaccga cgccccagca    2520
ctcgtccgag ggcaaaggaa tagagtagat gccgaccgaa caagagctga tttcgagaac    2580
gcctcagcca gcaactcgcg cgagcctagc aaggcaaatg cgagagaacg gccttacgct    2640
tggtggcaca gttctcgtcc acagttcgct aagctcgctc ggctgggtcg cgggagggcc    2700
ggtcgcagtg attcaggccc ttctggattg tgttggtccc cagggcacga ttgtcatgcc    2760
cacgcactcg ggtgatctga ctgatcccgc agattggaga tcgccgcccg tgcctgccga    2820
ttgggtgcag atctatttaa atgcgttaca taacttacgg taaatggccc gcctggctga    2880
ccgcccaacg accccgccc attgacgtca ataatgacgt atgttcccat agtaacgcca    2940 ataggactt tccattgacg tcaatggggtg gagtatttac ggtaaactgc ccacttggca    3000
gtacatcaag tgtatcatat gccaagtacg cccctattg acgtcaatga cggtaaatgg    3060
cccgcctggc attatgccca gtacatgacc ttatgggact ttcctacttg gcagtacatc    3120
tacgtattag tcatcgctat taccatgatt taaatgctgg gactacagga gcttgttacc    3180
acacccagct ccagtttata aattcatctc cagtttataa aggaggaaac cgaggtactg    3240
agaggttaaa aaaccttcct gcagacactt gtccagcaag tggccactcc aggatttgga    3300
ccaaggtgat gtgtcttcag gctgtgtctc tgccactgtg ccacgctgct gggtggtagg    3360
cagcagtggg tgggtgcctg cagtggtctg taaagaccac ctgagatgtc cttcctcctc    3420
tgttccaccc tgtccaggtc caagaagaca gtctatgaag agagagcagg tgtgactctc    3480
tcagtgtgct cctctgtgag aagcaggctg acatcccaaa gggaagggcg gataacagag    3540
acagtgcaag cggaggagat gagggtgcct caaagccggg aggctgggtg atgcaggagc    3600
ctgcgtgtcc cgaggggggt gctgggccca gtgtgagtac gtgtgactgt gactgagaca    3660
gtgtgactgc tgaaggcagg gacacagcag ctccctgact gggggcagaa ggcgttaact    3720
gtgtgaaggc tggttgtggg tgggtgggct ctgggcctcg aacccggggg ctgagggaga    3780
tagtaaacag cagggtgact gacgggaaga tcatgttggt agccctgcga agatgctgca    3840
gggctgtggg ggtttgtgtg actttgcagt tcaacaaatt caaattcagc caacgctggc    3900
```

```
agggcctgtt gtgccaggca accagctagg aggaggagac tcggacccag cttgcagctg    3960
aagggcgctg gctgccgggt tctgtgggtt caccttgcgg tgtcttccct tgctaacact    4020
gagtccttac aatagcccca tctccaggtt gaggctagat ggaggggaca gagggaagtg    4080
acttgcccaa ggtgacccaa gctcccgagt gccagggcag gatctgaatt caggctctca    4140
gactgcagag cctgagtccc tccctgccat gcctgtgcca gggtggaaat gtctggtcct    4200
ggaggggagc gtggactcct ggccttggct ctggagacat cccctagac cacgtgggct     4260 cctaacctgt ccatggtcac tgtgctgagg ggcgggacgg tgggtcaccc ctagttcttt    4320 tttcccagg gccagattca tggactgaag ggttgctcgg ctctcagaga cccctaagc      4380 gccccgccct ggccccaagc cctcccccag ctcccgcgtc ccccccctcc tggcgctgac    4440
tccgggccag aagaggaaag gctgtctcca cccacctctc gcactctccc ttctccttta   4500
taaaggccgg aacagctgaa agggtggcaa cttctcctcc tgcagccggg agcggcctgc   4560
ctgcctccct gcgcacccgc agcctccccc gctgcctccc tagggctccc ctccggccgc   4620
cagcgcccat ttttcattcc ctagatagag atactttgcg cgcacatcga tatgctgccc   4680
ggtttggcac tgctcctgct ggccgcctgg acggctcggg cgctggaggt acccactgat   4740
ggtaatgctg gcctgctggc tgaaccccag attgccatgt tctgtggcag actgaacatg   4800
cacatgaatg tccagaatgg gaagtgggat tcagatccat cagggaccaa aacctgcatt   4860
gataccaagg aaggcatcct gcagtattgc caagaagtct accctgaact gcagatcacc   4920
aatgtggtag aagccaacca accagtgacc atccagaact ggtgcaagcg gggccgcaag   4980
cagtgcaaga cccatcccca ctttgtgatt ccctaccgct gcttagttgg tgagtttgta   5040
agtgatgccc ttctcgttcc tgacaagtgc aaattcttac accaggagag gatggatgtt   5100
tgcgaaactc atcttcactg gcacaccgtc gccaaagaga catgcagtga aagagtacc    5160 aacttgcatg actacggcat gttgctgccc tgcggaattg acaagttccg aggggtagag   5220
tttgtgtgtt gcccactggc tgaagaaagt gacaatgtgg attctgctga tgcggaggag   5280
gatgactcgg atgtctggtg gggcggagca gacacagact atgcagatgg gagtgaagac   5340
aaagtagtag aagtagcaga ggaggaagaa gtggctgagg tggaagaaga agaagccgat   5400
gatgacgagg acgatgagga tggtgatgag gtagaggaag aggctgagga accctacgaa   5460
gaagccacag agaaccacc cagcattgcc accaccacca ccaccaccac agagtctgtg    5520
gaagaggtgg ttcgagttcc tacaacagca gccagtaccc ctgatgccgt tgacaagtat   5580
ctcgagacac ctggggatga gaatgaacat gcccatttcc agaaagccaa agagaggctt   5640
gaggccaagc accgagagag aatgtcccag gtcatgagag aatgggaaga ggcagaacgt   5700
caagcaaaga acttgcctaa agctgataag aaggcagtta ccagcatttt ccaggagaaa   5760
gtggaatctt tggaacagga agcagccaac gagagacagc agctggtgga gacacacatg   5820
gccagagtgg aagccatgct caatgaccgc cgccgcctgg ccctggagaa ctacatcacc   5880
gctctgcagg ctgttcctcc tcggcctcgt cacgtgttca atatgctaaa gaagtatgtc   5940
cgcgcagaac agaaggacag acagcacacc ctaaagcatt tcgagcatgt gcgcatggtg   6000
gatcccaaga aagccgctca gatccggtcc caggttatga cacacctccg tgtgatttat   6060
gagcgcatga atcagtctct ctccctgctc tacaacgtgc ctgcagtggc cgaggagatt   6120
caggatgaag ttgatgagct gcttcagaaa gagcaaaact attcagatga cgtcttggcc   6180
aacatgatta gtgaaccaag gatcagttac ggaaacgatg ctctcatgcc atcttttgacc   6240 gaaacgaaaa ccaccgtgga gctccttccc gtgaatggag agttcagcct ggacgatctc   6300
```

```
cagccgtggc attcttttgg ggctgactct gtgccagcca acacagaaaa cgaagttgag   6360
cctgttgatg cccgccctgc tgccgaccga ggactgacca ctcgaccagg ttctggggttg  6420 acaaatatca agacggagga gatctctgaa gtgaatctgg atgcagaatt ccgacatgac   6480
tcaggatatg aagttcatca tcaaaaattg gtgttctttg cagaagatgt gggttcaaac   6540
aaaggtgcaa tcattggact catggtgggc ggtgttgtca tagcgacagt ggtcatcatc   6600
accttggtga tgctgaagaa gaaacagtac acatccattc atcatggtgt ggtggaggtt   6660
gacgccgctg tcaccccaga ggagcgccac ctgtccaatc tgcagcagaa cggctacgaa   6720
aatccaacct acaagttctt tgagcagatg cagaacttaa ttaaggcatg cggaagcgga   6780
gctactaact tcagcctgct gaagcaggct ggagacgtgg aggagaaccc tggacctaga   6840
tctatggctg agccccgcca ggagttcgaa gtgatggaag atcacgctgg gacgtacggg   6900
ttgggggaca ggaaagatca gggggggctac accatgcacc aagaccaaga gggtgacacg   6960
gacgctggcc tgaaagctga agaagcaggc attggagaca ccccccagcct ggaagacgaa   7020 gctgctggtc acgtgaccca agctcgcatg gtcagtaaaa gcaaagacgg gactggaagc   7080
gatgacaaaa aagccaaggg ggctgatggt aaaacgaaga tcgccacacc gcggggagca   7140 gccccctccag gccagaaggg ccaggccaac gccaccagga ttccagcaaa accccgccc   7200 gctccaaaga caccacccag ctctggtgaa cctccaaaat caggggatcg cagcggctac   7260
agcagccccg gctccccagg cactcccggc agccgctccc gcaccccgtc ccttccaacc   7320
ccacccaccc gggagcccaa gaaggtggca gtggtccgta ctccacccaa gtcgccgtct   7380
tccgccaaga gccgcctgca gacagccccc gtgcccatgc cagacctgaa gaatgtcaag   7440
tccaagatcg gctccactga gaacctgaag caccagccgg gaggcgggaa ggtgcagata   7500
attaataaga agctggatct tagcaacgtc cagtccaagt gtggctcaaa ggataatatc   7560
aaacacgtcc tgggaggcgg cagtgtgcaa atagtctaca accagttgga cctgagcaag   7620
gtgacctcca agtgtggctc attaggcaac atccatcata aaccaggagg tggccaggtg   7680
gaagtaaaat ctgagaagct tgacttcaag gacagagtcc agtcgaagat tgggtccctg   7740
gacaatatca cccacgtccc tggcggagga aataaaaaga ttgaaaccca caagctgacc   7800
ttccgcgaga cgccaaagc caagacagac cacggggcgg agatcgtgta caagtcgcca   7860
gtggtgtctg gggacacgtc tccacggcat ctcagcaatg tctcctccac cggcagcatc   7920
gacatggtag actcgcccca gctcgccacg ctagctgacg aggtgtctgc ctccctggcc   7980
aagcagggtt tggaattcgg aagcggagct actaacttca gcctgctgaa gcaggctgga   8040
gacgtggagg agaaccctgg acctctcgag atgacagagt tacctgcacc gttgtcctac   8100
ttccagaatg cacagatgtc tgaggacaac cacctgagca atactgtacg tagccagaat   8160
gacaatagag aacggcagga gcacaacgac agacggagcc ttggccaccc tgagccatta   8220
tctaatggac gaccccaggg taactcccgg caggtggtgg agcaagatga ggaagaagat   8280
gaggagctga cattgaaata tggcgccaag catgtgatca tgctctttgt ccctgtgact   8340
ctctgcatgg tggtggtcgt ggctaccatt aagtcagtca gcttttatac ccggaaggat   8400
gggcagctaa tctatacccc attcacagaa gataccgaga ctgtgggcca gagagccctg   8460
cactcaattc tgaatgctgc catcatgatc agtgtcattg ttgtcctgac tatcctcctg   8520
gtggttctgt ataaatacag gtgctataag gtcatccatg cctggcttat tatatcatct   8580
ctattgttgc tgttcttttt ttcattcatt tacttggggg aagtgtttaa aacctataac   8640
```

```
gttgctgtgg actacattac tgttgcactc ctgatctgga attttggtgt ggtgggaatg      8700
atttccattc actggaaagg tccacttcga ctccagcagg catatctcat tatgattagt      8760
gccctcatgg ccctggtgtt tatcaagtac ctccctgaat ggactgcgtg gctcatcttg      8820
gctgtgattt cagtatatga tttagtggct gttttgtgtc cgaaaggtcc acttcgtatg      8880
ctggttgaaa cagctcagga gagaaatgaa acgcttttc cagctgtcat ttactcctca       8940
acaatggtgt ggttggtgaa tatggcagaa ggagacccgg aagctcaaag gagagtatcc      9000
aaaaattcca gtataatgc agaaagcaca gaaagggagt cacaagacac tgttgcagag       9060
aatgatgatg cgggttcag tgaggaatgg gaagcccaga gggacagtca tctagggcct       9120
catcgctcta cacctgagtc acgagctgct gtccaggaac tttccagcag tatcctcgct      9180
ggtgaagacc cagaggaaag gggagtaaaa cttggattgg gagatttcat tttctacagt      9240
gttctggttg gtaaagcctc agcaacagcc agtggagact ggaacacaac catagcctgt      9300
ttcgtagcca tattaattgg tttgtgcctt acattattac tccttgccat tttcaagaaa      9360
gcattgccag ctcttccaat ctccatcacc tttgggcttg ttttctactt tgccacagat      9420
tatcttgtac agccttttat ggaccaatta gcattccatc aattttatat ctagcctgca      9480
ggtctagata gctagcctcc ctatagtgag tcgtattacg tagatccaga catgataaga      9540
tacattgatg agtttggaca aaccacaact agaatgcagt gaaaaaaatg ctttatttgt      9600
gaaatttgtg atgctattgc tttatttgta accattataa gctgcaataa acaagttaac      9660
aacaacaatt gcattcattt tatgtttcag gttcagggg aggtgtggga ggttttttaa       9720
ttcgcggccg cctcgagaga tccctcagg atatagtagt ttcgcttttg cataggggagg     9780 gggaaatgta gtcttatgca atactcttgt agtcttgcaa catggtaacg atgagttagc      9840
aacatgcctt acaaggagag aaaaagcacc gtgcatgccg attggtggaa gtaaggtggt      9900
acgatcgtgc cttattagga aggcaacaga cgggtctgac atggattgga cgaaccactg      9960
aattccgcat tgcagagata ttgtatttaa gtgcctagct cgatacagca aacgcctatt    10020
gaccattcac cacattggtg tgcacctcca agcttgttaa ttcaccatgt ctagactgga    10080
caagagcaaa gtcataaacg cgctctctgga attactcaat ggagtcggta tcgaaggcct   10140
gacgacaagg aaactcgctc aaaagctggg agttgagcag cctaccctgt actggcacgt    10200
gaagaacaag cgggcctgc tcgatgccct gccaatcgag atgctggaca ggcatcatac     10260
ccacttctgc cccctggaag gcgagtcatg gcaagacttt ctgcggaaca acgccaagtc    10320
attccgctgt gctctcctct cacatcgcga cggggctaaa gtgcatctcg gcacccgccc    10380
aacagagaaa cagtacgaaa ccctggaaaa tcagctcgcg ttcctgtgtc agcaaggctt    10440
ctccctggag aacgcactgt acgctctgtc cgccgtgggc cactttacac tgggctgcgt    10500
attggaggaa caggagcatc aagtagcaaa agaggaaaga gagacaccta ccaccgattc    10560 tatgcccca cttctgagac aagcaattga gctgttcgac cggcagggag ccgaacctgc     10620 cttcctttc ggcctggaac taatcatatg tggcctggag aaacagctaa agtgcgaaag     10680
cggcgggccg gccgacgccc ttgacgattt tgacttagac atgctcccag ccgatgccct   10740
tgacgacttt gaccttgata tgctgcctgc tgacgctctt gacgattttg accttgacat    10800
gctccccggg taactaagta aggatcaaca tcgaattcga tttctgttcc tgttaatcaa    10860
cctctggatt acaaaatttg tgaaagattg actggtattc ttaactatgt tgctcctttt    10920
acgctatgtg gatacgctgc tttaatgcct ttgtatcatg ctattgcttc ccgtatggct    10980
ttcattttct cctccttgta taaatcctgg ttgctgtctc tttatgagga gttgtggccc    11040
```

```
gttgtcaggc aacgtggcgt ggtgtgcact gtgtttgctg acgcaacccc cactggttgg    11100
ggcattgcca ccacctgtca gctcctttcc gggactttcg ctttccccct ccctattgcc    11160
acggcggaac tcatcgccgc ctgccttgcc cgctgctgga caggggctcg gctgttgggc    11220
actgacaatt ccgtggtgtt gtcggggaag ctgacgtcct ttccatggct gctcgcctgt    11280
gttgccacct ggattctgcg cgggacgtcc ttctgctacg tcccttcggc cctcaatcca    11340
gcggaccttc cttcccgcgg cctgctgccg gctctgcggc ctcttccgcg tcttcgcctt    11400
cgccctcaga cgagtcggat ctcccttggg gccgcctccc cgcctgtttc gcctcgggct    11460
caatcactag tgaattcgat aaaataaaag attttattta gtctccagaa aaaggggga    11520 atgaaagacc ccacctgtag gtttggcaag ctagcttaag taacgccatt ttgcaaggca    11580
tggaaaaata cataactgag aatagagaag ttcagatcaa ggtcaggaac agatggaaca    11640
gctgaatatg ggccaaacag atatctgtg gtaagcagtt cctgccccgg ctcagggcca    11700
agaacagatg gaacagctga atatgggcca aacaggatat ctgtggtaag cagttcctgc    11760
cccggctcag ggccaagaac agatggtccc cagatgcggt ccagccctca gcagtttcta    11820
gagaaccatc agatgtttcc agggtgcccc aaggacctga atgaccctg tgccttattt    11880 gaactaacca atcagttcgc ttctcgcttc tgttcgcgcg cttctgctcc ccgagctcaa    11940
taaaagagcc cacaacccct cactcggggc gccagtcctc cgattgactg agtcgcccgg    12000
gtacccgtgt atccaataaa ccctcttgca gttgcatccg acttgtggtc tcgctgttcc    12060
ttgggagggt ctcctctgag tgattgacta cccgtcagcg gggtctttc atttgggggc    12120 tcgtccggga tcgggagacc cctgcccagg gaccaccgac ccaccaccgg gaggtaagct    12180
ggctgcctcg cgcgtttcgg tgatgacggt gaaaacctct gacacatgca gctcccggag    12240
acggtcacag cttgtctgta gcggatgcc gggagcagac aagcccgtca gggcgcgtca    12300
gcgggtgttg gcgggtgtcg gggcgcagcc atgacccagt cacgtagcga tagcggagtg    12360
tatactggct taactatgcg gcatcagagc agattgtact gagagtgcac catatgcggt    12420
gtgaaatacc gcacagatgc gtaaggagaa aataccgcat caggcgctct tccgcttcct    12480
cgctcactga ctcgctgcgc tcggtcgttc ggctgcggcg agcggtatca gctcactcaa    12540
aggcggtaat acggttatcc acagaatcag gggataacgc aggaaagaac atgtgagcaa    12600
aaggccagca aaaggccagg aaccgtaaaa aggccgcgtt gctggcgttt ttccataggc    12660
tccgcccccc tgacgagcat cacaaaaatc gacgctcaag tcagaggtgg cgaaacccga    12720
caggactata aagataccag gcgtttcccc ctggaagctc cctcgtgcgc tctcctgttc    12780
cgaccctgcc gcttaccgga tacctgtccg cctttctccc ttcgggaagc gtggcgcttt    12840
ctcatagctc acgctgtagg tatctcagtt cggtgtaggt cgttcgctcc aagctgggct    12900
gtgtgcacga accccccgtt cagcccgacc gctgcgcctt atccggtaac tatcgtcttg    12960
agtccaaccc ggtaagacac gacttatcgc cactggcagc agccactggt aacaggatta    13020
gcagagcgag gtatgtaggc ggtgctacag agttcttgaa gtggtggcct aactacggct    13080
acactagaag gacagtattt ggtatctgcg ctctgctgaa gccagttacc ttcggaaaaa    13140
gagttggtag ctcttgatcc ggcaaacaaa ccaccgctgg tagcggtggt ttttttgttt    13200
gcaagcagca gattacgcgc agaaaaaaag gatctcaaga agatcctttg atcttttcta    13260
cggggtctga cgctcagtgg aacgaaaact cacgttaagg gattttggtc atgagattat    13320
caaaaaggat cttcacctag atcctttta attaaaaatg aagttttaaa tcaatctaaa    13380
```

```
gtatatatga gtaaacttgg tctgacagtt accaatgctt aatcagtgag gcacctatct    13440
cagcgatctg tctatttcgt tcatccatag ttgcctgact ccccgtcgtg tagataacta    13500
cgatacggga gggcttacca tctggcccca gtgctgcaat gataccgcga gacccacgct    13560
caccggctcc agatttatca gcaataaacc agccagccgg aagggccgag cgcagaagtg    13620
gtcctgcaac tttatccgcc tccatccagt ctattaattg ttgccgggaa gctagagtaa    13680
gtagttcgcc agttaatagt ttgcgcaacg ttgttgccat tgctgcaggc atcgtggtgt    13740
cacgctcgtc gtttggtatg gcttcattca gctccggttc ccaacgatca aggcgagtta    13800
catgatcccc catgttgtgc aaaaaagcgg ttagctcctt cggtcctccg atcgttgtca    13860
gaagtaagtt ggccgcagtg ttatcactca tggttatggc agcactgcat aattctctta    13920
ctgtcatgcc atccgtaaga tgcttttctg tgactggtga gtactcaacc aagtcattct    13980
gagaatagtg tatgcggcga ccgagttgct cttgcccggc gtcaacacgg ataataccg     14040 cgccacatag cagaacttta aaagtgctca tcattggaaa acgttcttcg gggcgaaaac    14100
tctcaaggat cttaccgctg ttgagatcca gttcgatgta acccactcgt gcacccaact    14160
gatcttcagc atctttact ttcaccagcg tttctgggtg agcaaaaaca ggaaggcaaa    14220
atgccgcaaa aaagggaata agggcgacac ggaaatgttg aatactcata ctcttccttt    14280
ttcaatatta ttgaagcatt tatcagggtt attgtctcat gagcggatac atatttgaat    14340
gtatttagaa aaataaacaa ataggggttc gcgcacatt tccccgaaaa gtgccacctg     14400
acgtctaaga aaccattatt atcatgacat taacctataa aaataggcgt atcacgaggc    14460
cctttcgtct tcaagaattc ataccagatc accgaaaact gtcctccaaa tgtgtccccc    14520
tcacactccc aaattcgcgg gcttctgcct cttagaccac tctaccctat tccccacact    14580
caccggagcc aaagccgcgg cccttccgtt tctttgct                            14618

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agatctattt aaataccggt                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgaggcgg ccgccctgca                                                20

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

```
ggatccattt aaatgctggg actacaggag cttg                                      34

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcgatgtgc gcgcaaagta tctcta                                               26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atcgatatgc tgcccggttt ggcact                                               26

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcatgctta attaagttct gcatctgctc aaaga                                     35

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agatctatgg ctgagccccg ccagga                                               26

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaattccaaa ccctgcttgg ccaggg                                               26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaattcggaa gcggagctac taactt                                               26
```

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctcgagaggt ccagggttct cctcca                                          26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctcgagatga cagagttacc tgcacc                                          26

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tctagacctg caggctagat ataaaattga tgga                                 34

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atttaaatgc gttacataac ttacgg                                          26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atttaaatca tggtaatagc gatgac                                          26

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gagatctctg aagtgaatct ggatgcagaa ttccga                               36

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcggaattct gcatccagat tcacttcaga gatctc                                36

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtcatagcga cagtggtcat catcaccttg gtgatg                                36

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
catcaccaag gtgatgatga ccactgtcgc tatgac                                36

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aatatcaaac acgtcctggg aggcggcagt gtgc                                  34

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cacactgccg cctcccagga cgtgtttgat att                                   33

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agtgtcattg ttgtcctgac tatcctcctg gtg                                   33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
caccaggagg atagtcagga caacaatgac act        33

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
tgaaacgctt tttccagctg tcatttactc ctcaaca        37

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
tgttgaggag taaatgacag ctggaaaaag cgtttca        37

<210> SEQ ID NO 34
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
agatctattt aaataccggt acgcgtatgc atttaattaa gtttaaacat gcatcctgca        60
gggcggccgc ctcgag        76

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gtgagtacgt gtgactgtga ctgag        25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gtcagtcacc ctgctgttta ctatc        25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aacctacaag ttctttgagc agatg                                      25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
atagatctag gtccagggtt ctcct                                      25

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
atctcagcaa tgtctcctcc ac                                         22

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
attctggcta cgtacagtat tgctc                                      25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gagtttggac aaaccacaac tagaa                                      25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gcaaaagcga aactactata tcctg                                      25

```
<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cttgacgatt ttgacttaga catgc                                          25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
taatccagag gttgattaac aggaa                                          25
```

EXPRESSION CASSETTE AND VECTOR COMPRISING ALZHEIMER'S DISEASE-RELATED MUTANT GENES AND CELL LINE TRANSFORMED BY MEANS OF SAME

SEQUENCE LISTING

The instant application contains a Sequence Listing which has been submitted electronically in ASCII format and is hereby incorporated by reference in its entirety. Said ASCII copy, created on Sep. 18, 2018, is named 103110-1300_SL.txt and is 48,293 bytes in size.

TECHNICAL FIELD

Embodiments relate to an expression cassette including a gene associated with an Alzheimer's disease (AD), a vector, and a cell line transformed using the vector. More particularly, the embodiments relate to an expression cassette including a mutant amyloid precursor protein (APP) gene, a mutant tau protein gene and a mutant presenilin 1 (PS1) gene so that the above mutant genes may be simultaneously expressed, relate to a cell line transformed using the expression cassette or a vector, and relate to an animal model transformed using the vector or the cell line.

BACKGROUND ART

An Alzheimer's disease (AD) is a kind of degenerative brain diseases and is the cause of 60% of cases of dementia that leads to loss of cognitive ability due to a gradual degeneration of neurons. ADs are classified according to causes into familial ADs caused by genetic factors, and sporadic ADs that occur in a large number of patients even though exact causes of sporadic ADs are not known. When a brain tissue of a patient died from the AD is examined under a microscope, neuritic plaques (or senile plaques) and neurofibrillary tangles are observed as specific lesions. When the brain tissue is observed with naked eyes, signs of a global brain atrophy due to a loss of neurons are found.

The neuritic plaques are formed by accumulating proteins or dead cells outside cells, and include, as a main component, β-amyloid beta (Aβ) that denotes peptides of 42 or 43 amino acids. The neurofibrillary tangles are abnormal aggregates of hyperphosphorylated tau proteins in a cytoskeleton in a cell and look like balls of yarn.

An amyloid precursor protein (APP) gene, a tau gene and a presenilin 1 (PS1) gene known as typical genes responsible for the AD have been known to contribute to overexpression of β-amyloid and aggregation of a tau protein.

β-amyloid is generated by a proteolysis from an APP. The APP is a protein with a single transmembrane domain, is expressed as a few isotypes by alternative splicing, and is known to pass through two metabolic pathways in a cell. In one of the two metabolic pathways, p3 and sAPPα are generated by α-secretase and γ-secretase. In the other, β-amyloid and APPβ are generated by β-secretase and γ-secretase. In patients with the familiar AD, a mutation is found in the APP. Mutations, for example, a Swedish APP670/671 mutation, a Flemish APP672 mutation, a Florida APP716 mutation, a London APP717 mutation, and the like have been found, and an increase in formation of β-amyloid has been found in the mutations.

Also, the PS1 gene represents a mutation that causes the familiar AD. A PS1 is a protein with eight transmembrane domains, plays an important role in a generation process, and is known to act as γ-secretase or as a subunit of a γ-secretase complex. At least 45 mutations of the PS1 causing the familiar AD have been reported, and lead to an increase in an amount of β-amyloid to be formed.

The AD caused by generated β-amyloid leads to a process of a damage to neurons due to hyperphosphorylation of a tau protein. It has been known that a few phosphoenzymes act for the hyperphosphorylation of the tau protein. Due to formation of tangles of the tau protein in addition to the hyperphosphorylation of the tau protein, neurons are damaged. A mutation of the tau protein in which tangles are properly formed has been found.

Revealing of a tangle formation mechanism of a tau protein, and accumulation and aggregation of β-amyloid in addition to aging of human brain cells may be expected to play an important role in a treatment of the AD. Thus, there is a desire for a necessity to establish an animal model or a cell line in which an APP gene mutation, a PS1 gene mutation and a tau gene mutation are simultaneously expressed.

In various studies, attempts have been made to establish a transgenic mouse, to study a pathogenesis of the AD. A transgenic gene that is a main goal of the above attempts may include, for example, ApoE4, and an APP gene, a PS1 gene and a tau gene known as genes responsible for the familiar AD. A transgenic mouse that is being mainly used in a current study is a model to form neuritic plaques by increasing a concentration of β-amyloid in a brain using a mutation in an APP gene or a PS1 gene. However, since it is difficult to accurately know the pathogenesis of the AD based on only β-amyloid, attempts are being made to simultaneously insert mutant genes of a tau protein recently. The attempts are made to create a model more similar to a human AD by simultaneously expressing β-amyloid and the tau protein in a brain of a transgenic mouse.

When both a mutant APP gene and a mutant PS1 gene are present, β-amyloid may be generated even earlier. A phenomenon in which β-amyloid is accumulated in a brain of a first-generation transgenic mouse TG2576 begins after the transgenic mouse TG2576 is raised during at least 12 months, whereas an accumulation of β-amyloid is started within six months after a birth of a transgenic mouse 5XFAD or APP/PS1. A double transgenic mouse generated by mating a single APP transgenic mouse and a single PS1 transgenic mouse is being used in a variety of research, since 1996 when Duff succeeded in developing the double transgenic mouse. Actually, due to a synergistic effect of two genes in a double transgenic mouse, a spot is observed to be formed three months to nine months earlier. However, since most of double transgenic mice are obtained by mating an APP transgenic mouse and a PS1 transgenic mouse, expression of each gene is independently controlled from each promoter and used promoters are not expressed specifically to only neurons in numerous cases. Thus, it is difficult to conduct studies on the pathogenesis of the AD. In addition, metabolism of a mouse that is a rodent is greatly different from metabolism of a human, which may show a great difference in evaluation of effectiveness in development of medications for ADs.

To solve the above issues, AD mutant genes may be present in a single chromosome and may need to be completely linked and inherited to a next generation. Also, there is a desire for a necessity to use an animal that is very similar to a human and that may be freely transformed among non-rodents.

DISCLOSURE OF INVENTION

Technical Goals

An aspect is to provide an expression cassette including a mutant amyloid precursor protein (APP) gene, a mutant tau protein gene and a mutant presenilin 1 (PS1) gene that are associated with an Alzheimer's disease (AD) so that the mutant APP gene, the mutant tau gene and the mutant PS1 gene are simultaneously expressed.

Another aspect is to provide an expression vector including the expression cassette.

Still another aspect is to provide a cell line transformed using the expression vector and an animal model transformed using the expression vector.

Technical Solutions

According to an aspect, there is provided an expression cassette associated with an Alzheimer's disease (AD), the expression cassette including a) a mutant amyloid precursor protein (APP) gene for encoding an APP, b) a mutant tau gene for encoding a tau protein, c) a mutant presenilin 1 (PS1) gene for encoding a PS1 and d) a neuron-specific promoter for controlling the mutant APP gene, the mutant tau gene and the mutant PS1 gene all at once.

The neuron-specific promoter may be a human platelet-derived growth factor (hPDGF) β-chain promoter, and may have a sequence of SEQ ID NO: 2.

The expression cassette may further include a cytomegalovirus (CMV) enhancer.

The CMV enhancer may have a sequence of SEQ ID NO: 3.

The mutant APP gene may have a mutation at amino acid position 595, amino acid position 596, or both. The mutant APP gene may have a sequence of SEQ ID NO: 4.

The mutant tau gene may have a mutation at amino acid position 243. The mutant tau gene may have a sequence of SEQ ID NO: 5.

The mutant PS1 gene may have a mutation at amino acid position 146, amino acid position 286, or both. The mutant PS1 gene may have a sequence of SEQ ID NO: 6.

The expression cassette may further include a 2A sequence between the mutant APP gene and the mutant tau gene and a 2A sequence between the mutant tau gene and the mutant PS1 gene.

The 2A sequences may each have a sequence of SEQ ID NO: 8.

According to another aspect, there is provided a recombinant expression vector including the expression cassette.

The recombinant expression vector may have a sequence of SEQ ID NO: 9.

According to another aspect, there is provided a cell line transformed using the recombinant expression vector.

According to another aspect, there is provided an animal other than a human, the animal being transformed using the recombinant expression vector or the cell line.

The animal may be a mammal.

The animal may be a pig.

According to another aspect, there is provided a method of manufacturing a recombinant expression vector, the method including constructing a first vector, the first vector that includes a restriction enzyme site and from which a promoter and a gene cluster are removed, inserting a promoter, an APP gene, a PS1 gene and a tau gene into a second vector, to obtain a recombinant second vector, inducing a mutation in each of the APP gene, the PS1 gene and the tau gene of the recombinant second vector, and inserting the recombinant second vector into the first vector.

Effect of the Invention

According to embodiments, a gene expression cassette, an expression vector, a transgenic cell line and a transgenic animal model may be provided to simultaneously adjust and express three Alzheimer's disease (AD)-related genes, for example, an amyloid precursor protein (APP) gene, a presenilin 1 (PS1) gene and a tau gene using a single gene-carrying vector and a single promoter, and may be used for research to find out a pathogenesis between the three AD-related genes. Also, since a disease occurs in the transgenic cell line or the transgenic animal model in a short period of time in comparison to an existing animal model, the transgenic cell line or the transgenic animal model may be more efficiently used to develop AD-related medications.

BRIEF DESCRIPTION OF DRAWINGS

FIG. 1B discloses SEQ ID NO: 34.

FIG. 4 is a diagram illustrating primers used to verify integration of a multi-cistronic vector of a pTet retrovirus. FIG. 4 discloses SEQ ID NOS 35-44, respectively, in order of appearance.

FIG. 7 is a table showing a result of a DNA fragment analysis of S0227, S0018 and SW316 among STR sites of each of a surrogate mother, a donor cell and cloned pigs.

BEST MODE FOR CARRYING OUT THE INVENTION

Figure 1A:
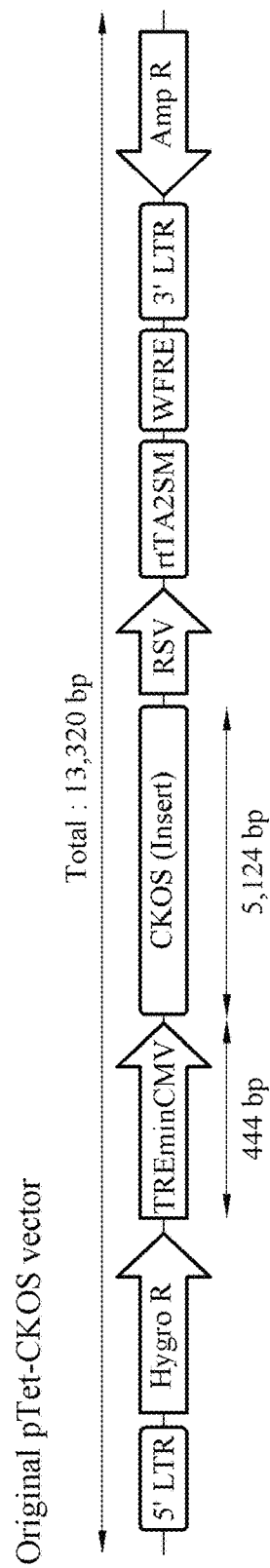
FIG. 1A is a diagram illustrating an original pTet CKOS retroviral vector.

Hereinafter, embodiments will be described in detail with reference to the accompanying drawings.

Embodiments may provide an expression cassette associated with an Alzheimer's disease (AD). The expression cassette may include a) a mutant amyloid precursor protein (APP) gene for encoding an APP, b) a mutant tau gene for encoding a tau protein, c) a mutant presenilin 1 (PS1) gene for encoding a PS1 and d) a neuron-specific promoter for controlling the mutant APP gene, the mutant tau gene and the mutant PS1 gene all at once.

The neuron-specific promoter may include, for example, all promoters enabling a gene to be specifically expressed in neurons, regardless of a type of promoters. For example, the neuron-specific promoter may be a human platelet-derived growth factor (hPDGF) β-chain promoter that has been known as a promoter to allow an exotic gene to be expressed in a brain cell of a pig.

The expression cassette may further include an enhancer to further enhance expression of a gene. The enhancer may include, for example, a cytomegalovirus (CMV) enhancer.

The expression cassette may further include 2A sequences between the mutant APP gene, the mutant tau gene and the mutant PS1 gene. For example, a 2A sequence may be inserted between the mutant APP gene and the mutant tau gene, and a 2A sequence may be inserted between the mutant tau gene and the mutant PS1 gene.

A 2A gene sequence according to an embodiment may code 18 to 22 amino acids. Among the amino acids, four amino acids located in a terminal, that is, asparagine (N), proline (P), glycine (G) and proline (P), are importantly preserved between species. The 2A gene sequence tends to self-cleave in synthesis of peptide. Due to the above properties, when a ribosome reaches sites of genetic code encoding N, P, G located in a terminal of a 2A sequence during a protein transcription, the ribosome may sequentially recognize N, P, G and may form peptide bonds. The ribosome may bring a releasing factor (RF) instead of a prolyl-transfer ribonucleic acid (tRNA) on a site in which proline is encoded. When the RF is bonded, a peptide formed in advance may not be connected to the peptide bond any more, and may be discharged from the ribosome. A code encoded after the 2A sequence may operate normally to perform a next protein transcription. As a result, by inserting a 2A sequence, a plurality of genes may be expressed using a single promoter. According to an embodiment, the expression cassette may simultaneously express the above three genes by inserting 2A sequences between the three genes.

The mutant APP gene may have a mutation at amino acid position 595, amino acid position 596, or both, and the mutant tau gene may have a mutation at amino acid position 243. The mutant PS1 gene may have a mutation at amino acid position 146, amino acid position 286, or both. For example, the mutant APP gene may be a gene in which lysine (Lys) is mutated to asparagine (Asn) at amino acid position 595 in APP695 and methionine (Met) is mutated to Lys at amino acid position 596. The mutant tau gene may be a gene in which phenylalanine (Phe) is mutated to Lys at amino acid position 243. The mutant PS1 gene may be a gene in which Met is mutated to leucine (Leu) at amino acid position 146 and proline (Pro) is mutated to Leu at amino acid position 286.

The mutant APP gene may have a sequence of SEQ ID NO: 4 and the mutant tau gene may have a sequence of SEQ ID NO: 5. The mutant PSI gene may have a sequence of SEQ ID NO: 6.

Embodiments may provide a recombinant expression vector including the expression cassette. In the present disclosure, all expression vectors to induce efficient expression of an AD-related protein with specificity to neurons may be used regardless of a type of expression vectors, and a retroviral vector may desirably be used.

Also, embodiments may provide a cell line transformed using the recombinant expression vector, and provide an animal that is other than a human and that is transformed using the cell line.

The cell line may include, for example, cell lines of animals derived from mammals other than a human with a limitation. However, since a commonly used mouse has an extremely high metabolic rate and a change in a life cycle of the mouse is completely different from that of a human, it has been difficult to use the mouse as an accurate disease model. Thus, an animal having a size similar to a body size of a human and similar in metabolism to the human may desirably be used, and most desirably, a pig may be used. When a pig transformed using a mutant gene of an AD produced according to an embodiment is used, there is an advantage in that studies on actions of three genes associated with the AD may be simultaneously conducted by simultaneously creating the three genes. In particular, research on a change in a nervous system as a problem in the AD by neuron-specific expression may be focused.

Hereinafter, the present disclosure will be described in detail with reference to examples. The examples are merely intended for the purpose of describing the present disclosure, and the scope of the present disclosure is not limited or restricted to the examples.

EXAMPLE 1

Construction of New Retroviral Vector

A tetracycline (Tet) responsive element (TRE) minimal CMV promoter and a CKOS gene cluster were eliminated from pTet-CKOS that is a retroviral vector. The retroviral vector was modified to have restriction enzyme sites, for example, BglII, SwaI, PacI, NotI and XhoI, to be advantageous for gene cloning.

FIG. 1A is a diagram illustrating an original pTet CKOS retroviral vector.

Figure 1B:
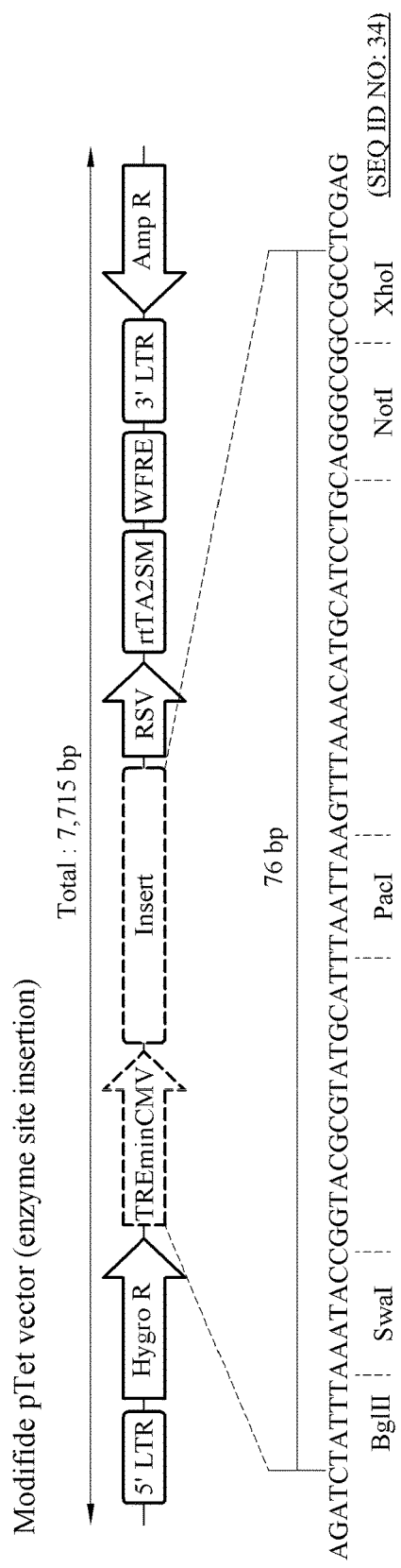
FIG. 1B is a diagram illustrating a modified pTet vector.

FIG. 1B is a diagram illustrating a modified pTet vector.

Referring to FIGS. 1A and 1B, the TRE minimal promoter and a CKOS part (5,568 base pairs (bp)) were eliminated from the original pTet-CKOS vector with a total length of 13,320 bp, and a multiple cloning site of 76 bp was inserted in a site in which the TRE minimal promoter and the CKOS part were eliminated. An example of a base sequence of the pTet vector with a modified structure may be defined with reference to SEQ ID NO: 1 described in the accompanying sequence list.

EXAMPLE 2

Introduction of CMV Enhancer, hPDGF Promoter and AD Gene

A primer including a restriction enzyme site was manufactured and used to insert, into a vector, an hPDGF promoter, a CMV enhancer, and an APP gene (NM_201414.2) of a β-amyloid, a PS1 gene (NM_000021.3), a tau gene (NM_016834.4), and the like that cause the AD.

TABLE 1

| Target | Primer name | Sequence (5' -> 3') | Size |
|---|---|---|---|
| pTet-enz. insert | pTet-Enz-insert-F | AGATCTATTTAAATACCGGT (SEQ ID NO: 10) | 67 bp |
| | pTet-Enz-insert-R | CTCGAGGCGGCCGCCCTGCA (SEQ ID NO: 11) | |

TABLE 1-continued

| Target | Primer name | Sequence (5' -> 3') | Size |
|---|---|---|---|
| hPDGFb promoter | BamH1-Swa1-PDGFb-F | GGATCCATTTAAATGCTGGGACTACAGGA GCTTG (SEQ ID NO: 12) | 1,530 bp |
|  | PDGFb-Cla1-R | ATCGATGTGCGCGCAAAGTATCTCTA (SEQ ID NO: 13) |  |
| hAPPswcDNA | Cla1-hAPPsw-F | ATCGATATGCTGCCCGGTTTGGCACT (SEQ ID NO: 14) | 2,106 bp |
|  | hAPPsw-Pac1-Sph1-R | GGCATGCTTAATTAAGTTCTGCATCTGCT CAAAGA (SEQ ID NO: 15) |  |
| hTaucDNA | Bgl2-hTau-F | AGATCTATGGCTGAGCCCCGCCAGGA (SEQ ID NO: 16) | 1,161 bp |
|  | hTau-EcoR1-R | GAATTCCAAACCCTGCTTGGCCAGGG (SEQ ID NO: 17) |  |
| 2A peptide | EcoR1-2A-F | GAATTCGGAAGCGGAGCTACTAACTT (SEQ ID NO: 18) | 78 bp |
|  | 2A-Xho1-R | CTCGAGAGGTCCAGGGTTCTCCTCCA (SEQ ID NO: 19) |  |
| hPS1 cDNA | Xho1-hPS1-F | CTCGAGATGACAGAGTTACCTGCACC (SEQ ID NO: 20) | 1,424 bp |
|  | hPS1-Xba1-R | TCTAGACCTGCAGGCTAGATATAAAATTG ATGGA (SEQ ID NO: 21) |  |
| CMV enhancer | CMVE-F | ATTTAAATGCGTTACATAACTTACGG (SEQ ID NO: 22) | 321 bp |
|  | CMVE-R | ATTTAAATCATGGTAATAGCGATGAC (SEQ ID NO: 23) |  |

Table 1 shows used primers.

The CMV enhancer and PDGF promoter were hybridized and used as a promoter so that AD-related genes are overexpressed with specificity to brain neurons. Before constructing a retroviral vector as a final vector, each mutant gene, the CMV enhancer and PDGF promoter were inserted into a psCMV vector. To insert a gene into a psCMV vector, a polymerase chain reaction (PCR) was used for amplification and cloning was performed using a restriction enzyme site introduced into a vector.

Figure 2:
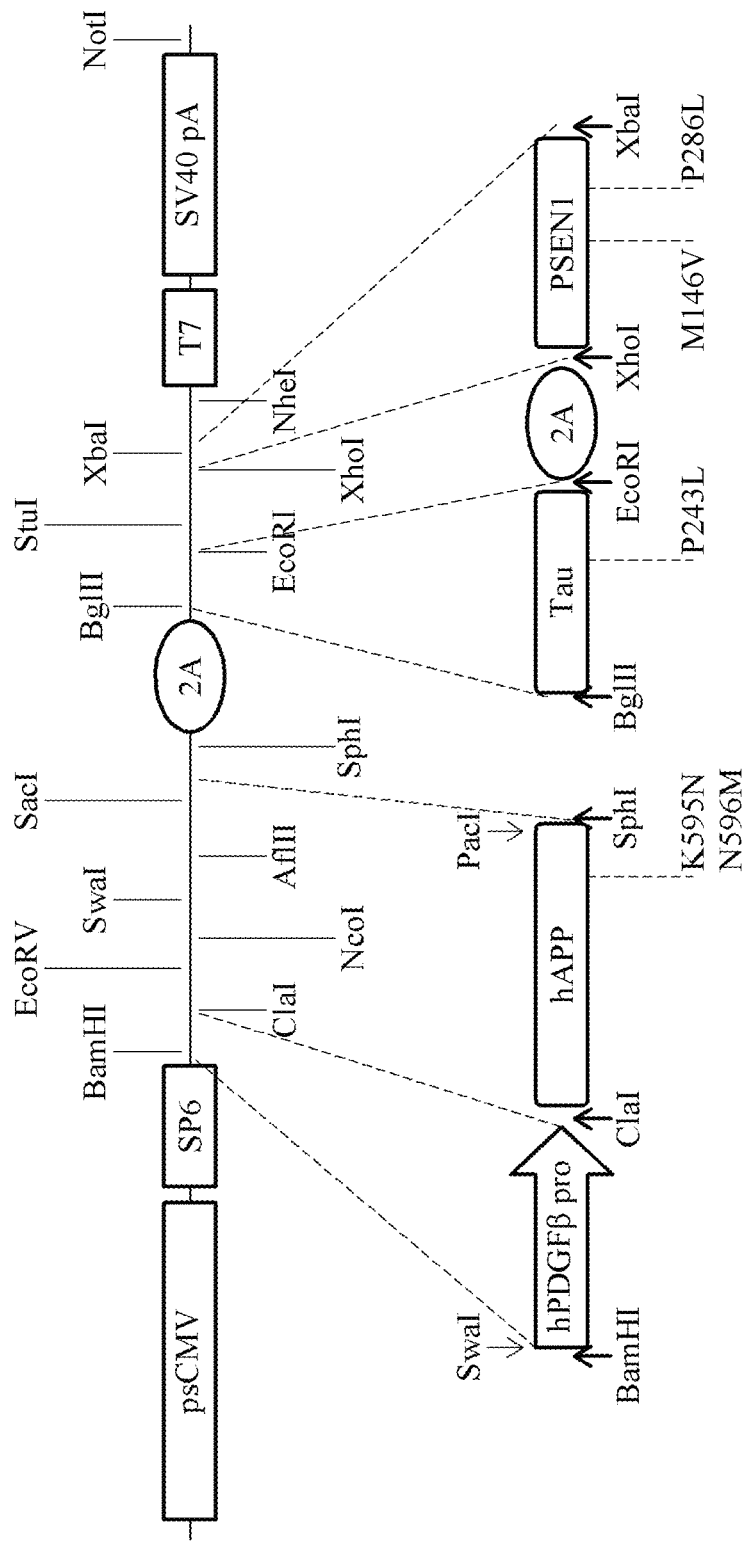
FIG. 2 is a diagram illustrating a structure of a psCMV vector including a human platelet-derived growth factor (hPDGF) β-chain promoter, a human amyloid precursor protein (hAPP) gene, a human tau (hTau) gene and a PSEN1 gene.

FIG. 2 is a diagram illustrating a structure of a psCMV vector including an hPDGFb promoter, a human APP (hAPP) gene, a human tau (hTau) gene and a PSEN1 gene manufactured according to an embodiment. An example of an SV40 poly A sequence may be defined with reference to SEQ ID NO: 7.

EXAMPLE 3

Mutagenesis of AD Gene

To induce a mutation in an amino acid of an AD related gene after inserting the AD related gene into a psCMV vector, a site-directed mutagenesis kit (Stratagene) was used.

TABLE 2

| Target | Primer name | Sequence (5' -> 3') |
|---|---|---|
| hAPPSw Mutagenesis-1 | hAPPsw-M1 (KM/NL)-F | GAGATCTCTGAAGTGAATCTGGATGCAGAATTCCGA (SEQ ID NO: 24) |
|  | hAPPsw-M1(KM/NL)-R | TCGGAATTCTGCATCCAGATTCACTTCAGAGATCTC (SEQ ID NO: 25) |
| hAPPSw Mutagenesis-2 | hAPPsw-M2(IV/VI)-F | GTCATAGCGACAGTGGTCATCATCACCTTGGTGATG (SEQ ID NO: 26) |
|  | hAPPsw-M2(IV/VI)-R | CATCACCAAGGTGATGATGACCACTGTCGCTATGAC (SEQ ID NO: 27) |
| hTau Mutagenesis | hTau-M(P/L)-F | AATATCAAACACGTCCTGGGAGGCGGCAGTGTGC (SEQ ID NO: 28) |
| hPS1 Mutagenesis-1 | hTau-M(P/L)-R | CACACTGCCGCCTCCCAGGACGTGTTTGATATT (SEQ ID NO: 29) |
|  | hPS1-M1(M/V)-F | AGTGTCATTGTTGTCCTGACTATCCTCCTGGTG (SEQ ID NO: 30) |
|  | hPS1-M1(M/V)-R | CACCAGGAGGATAGTCAGGACAACAATGACACT (SEQ ID NO: 31) |
| hPS1 Mutagenesis-2 | hPS1-M2(L/V)-F | TGAAACGCTTTTTCCAGCTGTCATTTACTCCTCAACA (SEQ ID NO: 32) |
|  | hPS1-M2(L/V)-R | TGTTGAGGAGTAAATGACAGCTGGAAAAAGCGTTT CA (SEQ ID NO: 33) |

Table 2 shows primers used for mutagenesis.

As an APP gene, an APP695 gene expressed in brain neurons was used, and double mutations were introduced at amino acid positions 595 and 596 in which familial mutations of the AD have been found. The mutations are known to form a larger amount of β-amyloid 42. The mutations are called "K595N" and "N596M." In a presenilin gene, two amino acid mutations were introduced. Mutations were introduced in amino acid positions 146 and 286 and are called "M146L" and "P286L," respectively. In a tau gene, a single mutation occurs at amino acid position 243 and is called "P243L."

To separate three mutant genes as independent peptides when the three mutant genes are translated to proteins after transcription to a single messenger RNA (mRNA), the three mutant genes are connected to each other by 2A sequences, as shown in FIG. 2.

EXAMPLE 4

Completion of Multi-Cistronic Vector of pTet Retrovirus

A psCMV vector in which a PDGF promoter and three mutant genes are connected in tandem was constructed, and was moved to the retroviral vector of Example 1 using restriction enzymes SwaI, PAcI and NotI, to complete a final recombinant expression vector. The completed recombinant expression vector was used to verify a deoxyribonucleic acid (DNA) sequence of 14,618 bp in total through a determination of a base sequence.

Figure 3A:
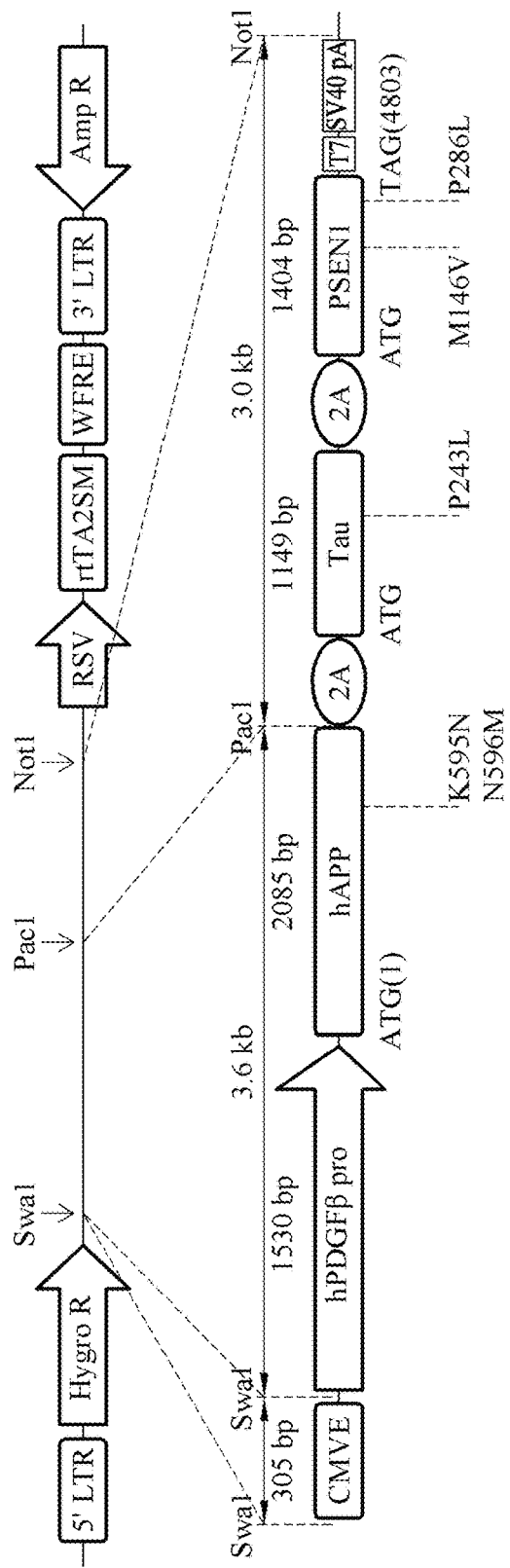
FIG. 3A is a diagram illustrating a one-dimensional (1D) structure of a multi-cistronic vector of a pTet retrovirus manufactured so that an hAPP gene, an hTau gene and a PSEN1 gene are expressed using a CMV enhancer and an hPDGF-β promoter.
Figure 3B:
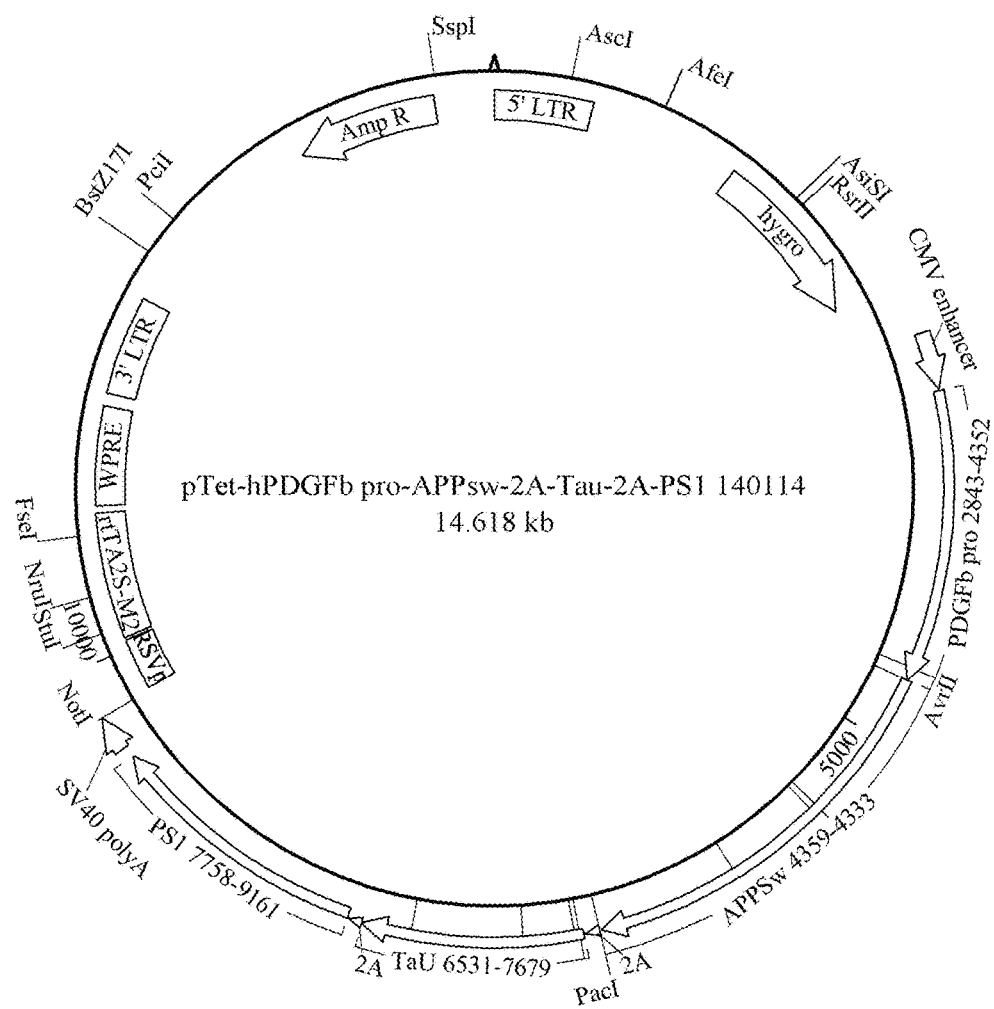
FIG. 3B is a diagram illustrating a cyclic structure of a multi-cistronic vector of a pTet retrovirus manufactured so that an hAPP gene, an hTau gene and a PSEN1 gene are expressed using a CMV enhancer and an hPDGF-β promoter.

FIG. 3A illustrates a one-dimensional (1D) structure of a multi-cistronic vector of a pTet retrovirus manufactured so that an hAPP gene, an hTau gene and a PSEN1 gene are expressed using a CMV enhancer and an hPDGF-β promoter, and FIG. 3B illustrates a cyclic structure of the multi-cistronic vector. As an example of the recombinant expression vector, a base sequence of pTet-CMVE-hPDGFb-APPsw-2A-Tau-2A-PS1 may be defined with reference to SEQ ID NO: 9 described in the accompanying sequence list.

EXAMPLE 5

Confirmation of Expression of Final Recombinant Expression Vector

A DNA preparation of the final recombinant expression vector was performed, a transfection of HT22 cells was performed using a Lipofectamine (Invitrogen), and whether three genes are simultaneously expressed in a cell was determined after 18 hours.

Expression of the three genes was confirmed based on a western blot scheme using an antibody of each of the three genes. Expression of an APP was detected based on antibodies 22C11 and 6E10. Expression of a tau protein was detected based on an antibody Tau5, and expression of a PS1 was detected based on a PS1-specific antibody.

After transient expression of the multi-cistronic vector of the pTet retrovirus in HEK-293 cells, a protein was detected using the western blot scheme. A 2A system properly operated in the recombinant expression vector.

EXAMPLE 6

Development of Pig Cell Line into Which AD Mutant Gene is Introduced

A DNA preparation of the final recombinant expression vector was performed, a transfection of ear cells of a pig was performed using an electroporation, and cell lines were selected by hygromycin. The electroporation was performed under a total of 11 conditions.

TABLE 3

| | | | | | | | | | | |
|---|---|---|---|---|---|---|---|---|---|---|
| | | | 3275 set parameters | | | | | | | |
| | | Poring Pulse (PP) | | | | Transfer Pulse (TP) | | | | |
| # | V | Time (ms) | Interval (ms) | Number of times | Decay rate (%) | V | Time (ms) | Interval (ms) | Number of times | Decay rate (%) | Polarity |
| 1 | Control group (with cells and DNA on which electroporation is not performed) | | | | | | | | | |
| 2 | 125 | 2.5 | 50 | 2 | 10 | 20 | 50 | 50 | 5 | 40 | +/− |
| 3 | 125 | 5 | 50 | 2 | 10 | 20 | 50 | 50 | 5 | 40 | +/− |
| 4 | 150 | 5 | 50 | 2 | 10 | 20 | 50 | 50 | 5 | 40 | +/− |
| 5 | 175 | 5 | 50 | 2 | 10 | 20 | 50 | 50 | 5 | 40 | +/− |
| 6 | 200 | 5 | 50 | 2 | 10 | 20 | 50 | 50 | 5 | 40 | +/− |
| 7 | 225 | 5 | 50 | 2 | 10 | 20 | 50 | 50 | 5 | 40 | +/− |
| 8 | 275 | 0.5 | 50 | 2 | 10 | 20 | 50 | 50 | 5 | 40 | +/− |
| 9 | 275 | 1 | 50 | 2 | 10 | 20 | 50 | 50 | 5 | 40 | +/− |
| 10 | 275 | 1.5 | 50 | 2 | 10 | 20 | 50 | 50 | 5 | 40 | +/− |
| 11 | 275 | 2 | 50 | 2 | 10 | 20 | 50 | 50 | 5 | 40 | +/− |

Table 3 shows conditions of the electroporation.

Cell lines were selected by continuously processing hygromycin (300 μg/mL) for five days under condition #5 (175 V, 5 ms) with a highest efficiency of expression and gene introduction. In the selected cell lines, whether three mutant genes were introduced into a chromosome was determined using a PCR.

FIG. 4 illustrates primers used in a PCR to verify integration of a multi-cistronic vector of a pTet retrovirus.

Figure 5:
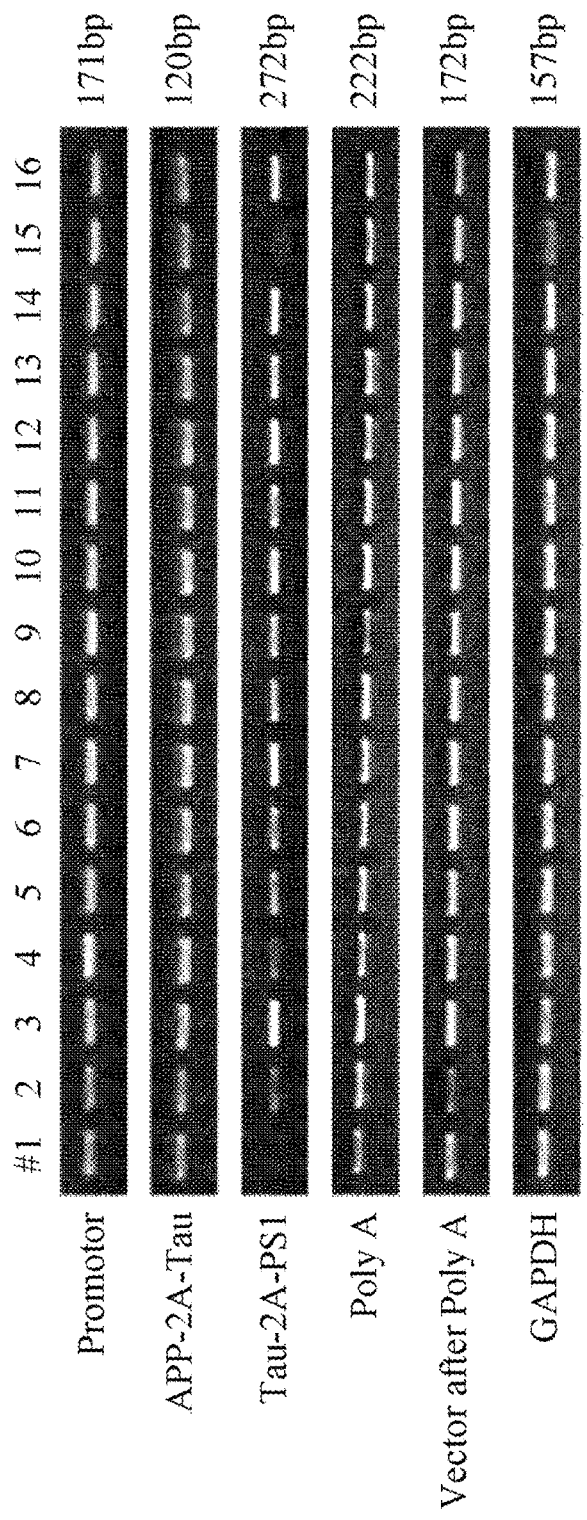
FIG. 5 is a photograph illustrating 16 cell lines of a pig based on a multi-cistronic vector of a pTet retrovirus.

FIG. 5 illustrates 16 cell lines of a pig using a multi-cistronic vector of a pTet retrovirus.

Cell lines were acquired from 16 colonies in total, respectively. It is found from FIG. 5 that all gene sites including a promoter site, mutant gene sites and a poly A site are integrated in a chromosome.

EXAMPLE 7

Analysis of Pig Cell Line into AD Mutant Gene is Introduced

The cell lines of Example 6 into which AD mutant genes are introduced were subcultured to increase a number of cells. By separating the cells, a stock was formed. Proteins were extracted from produced cell lines, and whether all three AD genes are expressed was determined.

Expression was detected based on the western blot scheme using the same antibodies as those used in Example 5.

It is found that all three proteins are expressed in the cell lines despite a difference in an amount of proteins to be expressed.

EXAMPLE 8

Production of AD Model Pig by Nuclear Substitution or DNA Injection

A fertilized egg transformed for production of an AD model pig was produced by a nuclear substitution or a DNA injection. To produce the fertilized egg using the nuclear substitution, a nucleus of an egg of a pig matured in vitro was removed from the egg, a transgenic cell containing an introduced AD gene directly was injected into the egg from which the nucleus was removed, and a cell fusion was performed in a solution of 0.3M mannitol (Sigma) using an LF201 Electro Cell Fusion Generator (NEPA GENE, Shioyaki, Japan) (at 120 volts (V) and 1 pulse 60 microseconds (μs)). Whether cells are fused was observed after 30 minutes, and the cells were processed for five hours in a culture medium, that is, a porcine zygote medium (PZM)-5 to which 7.5 mg/ml of cytochalasin B (sigma) was added.

To produce the fertilized egg using the DNA injection, an egg of a pig matured in vitro was fertilized in vitro by a fresh sperm of a pig for five hours (at a sperm concentration of 5,000 sperms per egg). When 18 hours have elapsed after the fertilization, fat globules were collected to one side by performing a centrifugation at a rate of 15,000 to 18,000 revolutions per minute (rpm) for ten minutes, and were fixed by a micromanipulator. A transgenic DNA with a concentration of 2 ng/ul was injected into pronuclei of the fertilized egg using an eppendorf femtojet.

A fertilized egg transformed using the nuclear substitution or the DNA injection was implanted into a surrogate mother, to produce an AD model pig. Typically, approximately 150 through 200 eggs were implanted per a single surrogate mother.

For the implantation, a pig in a preovulatory state was used to as a recipient pig. A primary ultrasonography was performed around 100 days after the implantation. A secondary ultrasonography was performed around 150 days after the implantation, and labor was induced performed around 180 days after the implantation, to produce an AD model pig.

An AD model pig born using the nuclear substitution has a weight of 568 grams (g) and a body length of 23 centimeters (cm), and is a female that is the same as a cell line.

EXAMPLE 9

Analysis of PCR to Determine Whether AD Model Pig is Transformed

A PCR was performed to determine whether an AD gene is expressed in a cloned pig produced using a somatic cell into which an AD gene is introduced. Each DNA was extracted from a tissue of the cloned pig, a tissue of a surrogate mother and a donor cell. The DNA was amplified using a primer for an AD-related gene, and an electrophoresis was performed.

A result obtained by analyzing whether AD-induced transformation was performed using a PCR indicates that the cloned pig has the same expression pattern as that of the donor cell and is determined as a pig transformed to induce an AD. The donor cell was used as a positive control.

EXAMPLE 10

Analysis of Parentage Test of AD Model Pig

To verify that a cloned pig born using the nuclear substitution of Example 8 is derived from a donor cell, a parentage test was analyzed. DNA was extracted from a tissue sample and a cell, and a sex chromosome X and four autosomal short tandem repeat (STR) sites, that is, S0226, S0227, S0018, and SW316 with a high polymorphism for each subject, were selected. DNA of each site was amplified using oligonucleotides with a fluorescent dye by a PCR, and a fragment analysis was performed using an automatic base sequence analyzing apparatus (ABI 3130xl Genetic Analyzer, Applied Biosystems).

Figure 6:
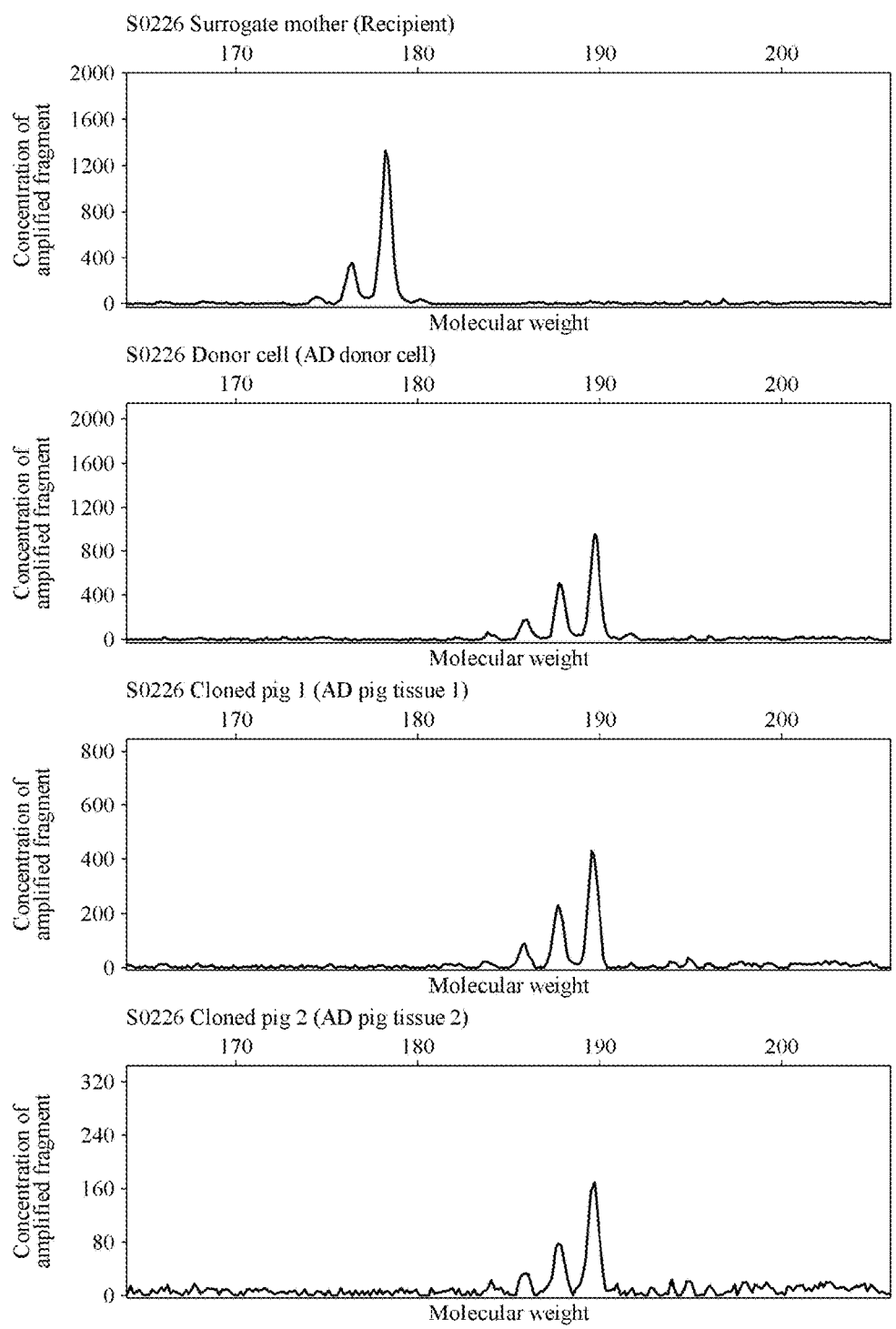
FIG. 6 illustrates a result of a deoxyribonucleic acid (DNA) fragment analysis of S0227 among short tandem repeat (STR) sites of each of a surrogate mother, a donor cell and cloned pigs.

FIG. 6 illustrates a result of a DNA fragment analysis of S0227 among STR sites of each of a surrogate mother, a donor cell and cloned pigs.

FIG. 7 is a table showing a result of a DNA fragment analysis of S0227, S0018 and SW316 among STR sites of each of a surrogate mother, a donor cell and cloned pigs.

The results of FIGS. 6 and 7 indicate that the clone pigs and the donor cell have the same genes in the four STR sites even though the surrogate mother shows a completely different gene pattern. Thus, it is found that a parent-child relationship between the surrogate mother and the cloned pigs is not formed and that the cloned pigs are derived from the donor cell and produced by the nuclear substitution.

The invention claimed is:

1. A recombinant expression vector comprising an expression cassette associated with an Alzheimer's disease (AD), the expression cassette comprising (a) a mutant amyloid precursor protein (APP) gene for encoding an APP, (b) a mutant tau gene for encoding a tau protein, (c) a mutant presenilin 1 (PS1) gene for encoding a PS1 and (d) a neuron-specific promoter for controlling the mutant APP gene, the mutant tau gene and the mutant PS1 gene all at once,
wherein the mutant APP gene, the mutant tau gene and the mutant PS1 gene are connected in tandem, and, wherein the recombinant expression vector comprises the sequence of SEQ ID NO: 9.

2. A transgenic mammalian cell line comprising the recombinant expression vector of claim 1.

3. A transgenic non-human mammal comprising the recombinant expression vector of claim 1.

4. The transgenic non-human mammal of claim 3, wherein the mammal is a pig.

5. A method of producing the recombinant expression vector of claim 1, the method comprising:
(i) constructing a pTet-CKOS derived first vector, the first vector comprising a restriction enzyme site insertion;
(ii) inserting a human platelet-derived growth factor (hPDGF)β-chain promoter, an amyloid precursor protein (APP) gene, a tau gene, and a presenilin 1 (PS1) gene into a psCMV vector, to obtain a recombinant second vector;
(iii) introducing a mutation in each of the APP gene, the tau gene, and the PS1 gene of the recombinant second vector; and
(iv) inserting an expression cassette comprising the hPDGF β-chain promoter, the mutant APP gene, the mutant tau gene, and the mutant PS1 gene which are connected in tandem, from the recombinant second vector into the first vector to produce the recombinant expression vector comprising the sequence of SEQ ID NO: 9 of claim 1.

* * * * *